United States Patent
Meng et al.

(10) Patent No.: US 9,643,968 B2
(45) Date of Patent: May 9, 2017

(54) FUSED ACRIDINE DERIVATIVE AND PHARMACEUTICAL COMPOSITION, PREPARATION METHOD AND USE THEREOF

(71) Applicant: Peking University, Beijing (CN)

(72) Inventors: Xiangbao Meng, Beijing (CN); Zhongjun Li, Beijing (CN); Shan Liu, Beijing (CN); Siwang Yu, Beijing (CN); Linling Que, Beijing (CN)

(73) Assignee: Peking University, Beijing (CN)

( * ) Notice: Subject to any disclaimer, the term of this patent is extended or adjusted under 35 U.S.C. 154(b) by 0 days.

(21) Appl. No.: 15/120,568

(22) PCT Filed: Feb. 15, 2015

(86) PCT No.: PCT/CN2015/073139
§ 371 (c)(1),
(2) Date: Aug. 22, 2016

(87) PCT Pub. No.: WO2015/127878
PCT Pub. Date: Sep. 3, 2015

(65) Prior Publication Data
US 2017/0015664 A1    Jan. 19, 2017

(30) Foreign Application Priority Data
Feb. 25, 2014    (CN) .......................... 2014 1 0065618

(51) Int. Cl.
C07D 471/06    (2006.01)
(52) U.S. Cl.
CPC .................. *C07D 471/06* (2013.01)
(58) Field of Classification Search
None
See application file for complete search history.

(56) References Cited

FOREIGN PATENT DOCUMENTS

| CN | 1036763 A | 11/1989 |
|---|---|---|
| WO | 0109133 A1 | 2/2001 |

OTHER PUBLICATIONS

Hao et al. In Journal of Organic Chemistry, 78(24), 12362-12373 (2013).*
International Search Report of PCT/CN2015/073139, dated Apr. 28, 2015.
Yoshiyasu Kitahara et al, Synthetic Studies of Benzo Pyrrolo, Teetrahedron, vol. 60, Dec. 31, 2004, pp. 1283-4288.
Wang, Qian et al, Synthesis and Crystal Structure of 4, 4-dimethyl-2 P-tolyl-4, 5-dihydro-2 H-pyrrolo, acridin, Journal of Jiangsu Normal University (Natural Science Edition), vol. 31, No. 3, Sep. 30, 2013, pp. 52-56.
Hao W.J. et al 12/02 Promoted Domino Reactions of Isatins or 3-Hydroxyindo-line-2-one Derivatives with Enaminones. J. Org. Chem, vol. 78, No. 24, Dec. 2, 2013, pp. 12362-12373.
Hassan Kefayati et al. An unexpected multicomponent reaction leading to 2-ar-ylpyrrolo [2, 3, 4-k] acridin-1 (2H) ones. Tetrahedron Letters, vol. 53, Jun. 19, 2012, pp. 4573-4575.
Wang H. Y. et al. An Efficieint Synthesis of Pyrrlol (2, 3, 4, kl) acridin-1-one Derivatives Catalyzed by L. Proline. Org. Lett., vol. 14, No. 17, Aug. 24, 2012 (Aug. 24, 2014) pp. 4598-4601.
Jiang B. et al. A domino synthetic strategy leading to two-carbon-tethered fused acridine/indole pairs and fused acridine derivatives. Org. Biomol. Chem. vol. 10, Sep. 7, 2012, pp. 8533-8538.

* cited by examiner

*Primary Examiner* — Dennis Heyer
(74) *Attorney, Agent, or Firm* — Banner & Witcoff, Ltd.

(57) ABSTRACT

Provided is a fused acridine derivative as formula (I), which has good antitumor activity. In addition, also provided are a process for preparing the derivative, a pharmaceutical composition containing the derivative, and the use thereof.

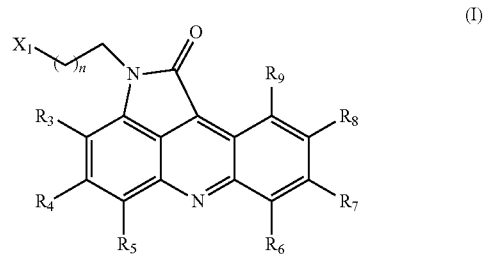

13 Claims, No Drawings

FUSED ACRIDINE DERIVATIVE AND PHARMACEUTICAL COMPOSITION, PREPARATION METHOD AND USE THEREOF

FIELD OF THE INVENTION

The invention relates generally to the field of medicinal chemistry, more specifically, relates to novel fused acridine derivatives, preparing processes, as well as pharmaceutical compositions and use thereof.

BACKGROUND OF THE INVENTION

The acridine was commercially used one century ago. 3,6-Diamino acridine was used against infections in clinical practice as early as in 1913. Until 1961, acridine began its anti-tumor journey after the concept of intercalation was proposed. Acridine is one of the privileged scaffolds of antitumor drugs for two reasons: one is the linear tricyclic aromatic structure of acridine ensures it is a good DNA intercalating agent; Second, modification of acridine, such as the side chain on the pyridine ring, resulting in various biologically active compounds with different mechanisms [Belmont. P.; Constant, J. F.; Demeunynck, M. Chem. Soc. Rev., 2001, 30, 70-81]; [Martinez, R.; Chacon-Garcia, L. Curr. Med. Chem., 2005, 12, 127-151]; [Belmont, P.; Dorange, I. Expert Opin. Ther. Patents, 2008, 18, 1211-1224].

Targets of acridine compounds included topoisomerase I/II, telomerase, tubulin, ABCG2/P-gP, and protein kinase, etc. Amsacrine (m-AMSA) and DACA were among the earliest acridine compounds for anti-tumor treatment, and also two typical topoisomerase inhibitors [Lagutschenkov, A.; Dopfer, O. J. Mol. Spectrosc., 2011, 268, 66-77]; [Cholewiski, G.; Dzierzbicka, K.; Koodziejczyk, A. M. Pharm. Rep., 2011, 63, 305-336]; [Kaur, J.; Singh P. Expert Opin. Ther. Pat., 2011, 21, 437-454].

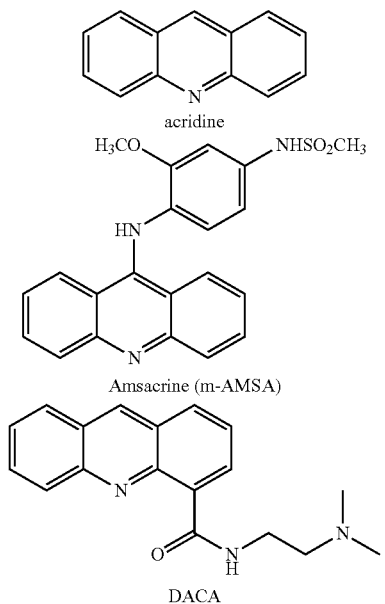

m-AMSA was used to treat leukemia in 1976, which was the first identified synthetic DNA intercalator and worked through the formation of DNA-topo II-intercalator triple complex. Now m-AMSA is used for the treatment of acute leukemia and malignant lymphoma, although shows low activity against solid tumors [Lang X. et al. Bioorg. Med. Chem. 2013, 21, 4170-4177]. DACA is topo I/topo II dual inhibitors [Crenshaw, J. M.; Graves, D. E.; Denny, W. A. Biochemistry 1995, 34, 13682-13687].

Moreover, miscellaneous dimer generated from acridine with other aromatic system via a polyamine linker would increase its affinity with DNA [Yang, X.-l.; Robinson, H.; Gao, Y.-G.; Wang, A. H. J. Biochemistry-US, 2000, 39(36), 10950-10957].

Huang and Shi et. al. disclosed a synthetic route to prepare pyrrolo[2,3,4-kl]acridin-1-(2H)-one [Wang, H.; Li, L.; Lin, W.; Xu, P.; Huang, Z.; Shi D. Org. Lett., 2012, 14, 4598-4601]. Subsequently, Wang and Ji reported the synthesis of similar compounds too [Hao, W-J.; Wang, J-Q.; Xu, X-P.; Zhang, S-L.; Wang, S-Y.; Ji, S-J. J. Org. Chem. 2013, 78, 12362-12373]. However, there were no biological activities involved.

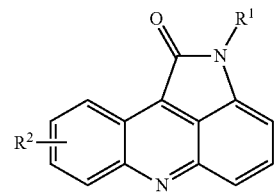

SUMMARY OF THE INVENTION

The present invention provides fused acridine derivatives with anticancer activities, which are prepared via a one-pot reaction from cyclohexane-1,3-dione, and isatin as raw materials.

The present invention also provides novel fused acridine derivatives, pharmaceutically acceptable acid addition salt, and solvate thereof.

The present invention also provides processes for preparing the fused acridine derivatives.

The present invention also provides the use of the fused acridine derivatives.

The invention also provides pharmaceutical compositions comprising the fused acridine derivatives.

The invention also provides the use of said pharmaceutical compositions.

The present invention also provides the use of the fused acridine derivatives or pharmaceutical compositions thereof for the treatment of tumors.

DETAILED DESCRIPTION OF THE INVENTION

In a first aspect, the present invention provides novel fused acridine derivatives of formula (I),

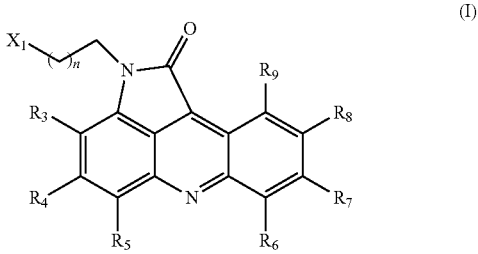

or pharmaceutically acceptable acid addition salt, or solvate thereof.

wherein, n is an integer from 0 to 6, preferably 1, 2, or 3;

$R_3$, $R_4$, $R_5$, $R_6$, $R_7$, $R_8$ and $R_9$ are each independently selected from the group consisting of hydrogen, hydroxyl, $C_1$-$C_4$ alkyl, $C_1$-$C_4$ alkoxyl, halogen, nitro and cyano; $X_1$ is hydroxyl or —$NR_1R_2$, wherein —$NR_1R_2$ is the following formula:

$R_1$ and $R_2$ are each independently selected from hydrogen, $C_1$-$C_4$ alkyl or substituted $C_1$-$C_4$ alkyl, $C_1$-$C_4$ alkylsulfonyl or $R_1$ and $R_2$ are taken together with the nitrogen to which they are attached to form a nitrogen-containing 4 to 6 membered heterocyclic ring;

wherein, the substituted $C_1$-$C_4$ alkyl refers to hydrogens of the alkyl are substituted by any number of the substituents selected from: hydroxyl, $C_1$-$C_4$ alkyl, halogen, nitro or cyano; said nitrogen-containing 4 to 6 membered heterocyclic rings are selected from nitrogen-containing 4, 5, and 6 membered heterocycles, which may be substituted with one or more of the substituents selected from hydroxyl, $C_1$-$C_4$ alkyl, $C_1$-$C_4$ alkoxyl, halogen, nitro or cyano; said nitrogen-containing 4, 5, or 6 membered heterocycles may be selected from azetidine, pyrrolidine, pyrrole, imidazole, piperidine, piperazine, or morpholine.

In some embodiments, the $C_1$-$C_4$ alkyl is optionally selected from methyl, ethyl, n-propyl, iso-propyl, n-butyl, iso-butyl, or t-butyl.

In some embodiments, the $C_1$-$C_4$ alkoxyl is optionally selected from methoxyl, ethoxyl, n-propoxyl, iso-propoxyl, n-butoxyl, iso-butoxyl, or t-butoxyl.

In some embodiments, the $C_1$-$C_4$ alkylsulfonyl is optionally selected from methanesulfonyl, ethanesulfonyl, n-propanesulfonyl, iso-propanesulfonyl, n-butanesulfonyl, iso-butanesulfonyl, or t-butanesulfonyl.

In some embodiments, the halogen is selected from the group consisting of fluoride, chloride, bromide, and iodide.

In one preferred embodiment, the present invention provides novel fused acridine derivatives of formula (I), wherein, $R_3$、$R_4$、$R_5$、$R_6$、$R_7$、$R_8$、and $R_9$ are each independently selected from hydrogen, hydroxyl, methyl, methoxyl, fluoro, chloro, bromo, iodo, nitro, or cyano; more preferably, $R_5$、$R_6$, and $R_8$ are each independently selected from hydrogen, hydroxyl, methyl, methoxyl, fluoro, chloro, bromo, iodo, nitro, or cyano, and $R_3$、$R_4$、$R_7$ and $R_9$ are each hydrogen.

In another preferred embodiment, the present invention provides novel fused acridine derivatives of formula (I), wherein, $X_1$ is hydroxyl, methanesulfonamido, —$N(CH_3)_2$, pyrrolidino, imidazolo, piperidino, piperazino, 4-methylpiperazino, or morpholino;

In some embodiments of the present invention provides novel fused acridine derivatives, the pharmaceutically acceptable acid addition salts are selected by inorganic acid addition salts or organic acid addition salts; wherein, said inorganic acid are selected from HCl, HBr, HI, $H_2SO_4$, and $H_3PO_4$; said organic acid are selected from methanesulfonic acid, benzenesulfonic acid, p-toluenesulfonic acid, maleic acid, fumaric acid, succinic acid, citric acid, and malic acid. The said solvate is hydrate.

In one preferred embodiment, the present invention provides a compound of formula (II):

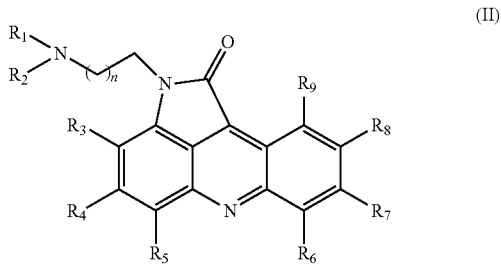

wherein, substituents of $R_1$、$R_2$、$R_3$、$R_4$、$R_5$、$R_6$、$R_7$、$R_8$、$R_9$, and n, are defined as those in formula (I).

In most preferred embodiments, the present invention provides one of the following compounds, or pharmaceutically acceptable acid addition salt, or solvate thereof:

2-(2-(dimethylamino)ethyl)pyrrolo[2,3,4-kl]acridin-1-(2H)-one (1a)

2-(3-morpholinopropyl)pyrrolo[2,3,4-kl]acridin-1-(2H)-one (1b)

2-(2-morpholinoethyl)pyrrolo[2,3,4-kl]acridin-1-(2H)-one (1d)

2-(2-(piperidin-1-yl)ethyl)pyrrolo[2,3,4-kl]acridin-1-(2H)-one (1f)

2-(2-(pyrrolidin-1-yl)ethyl)pyrrolo[2,3,4-kl]acridin-1-(2H)-one (1g)

2-(3-(pyrrolidin-1-yl)propyl)pyrrolo[2,3,4-kl]acridin-1-(2H)-one (1h)

2-(2-(dimethylamino)ethyl)-9-methylpyrrolo[2,3,4-kl]acridin-1-(2H)-one (2a)

9-chloro-2-(2-(dimethylamino)ethyl)pyrrolo[2,3,4-kl]acridin-1-(2H)-one (2b)

2-(2-(dimethylamino)ethyl)-9-methoxypyrrolo[2,3,4-kl]acridin-1-(2H)-one (2c)

2-(2-(dimethylamino)ethyl)-7-fluoropyrrolo[2,3,4-kl]acridin-1-(2H)-one (2d)

2-(2-(dimethylamino)propyl)-5-nitropyrrolo[2,3,4-kl]acridin-1-(2H)-one (2e)

2-(3-(dimethylamino)propyl)-9-methylpyrrolo[2,3,4-kl]acridin-1-(2H)-one (3a)

9-chloro-2-(3-(dimethylamino)propyl)pyrrolo[2,3,4-kl]acridin-1-(2H)-one (3b)

9-chloro-2-(3-(dimethylamino)propyl)pyrrolo[2,3,4-kl]acridin-1-(2H)-one fumarate (3b')

2-(3-(dimethylamino)propyl)-9-methoxypyrrolo[2,3,4-kl]acridin-1-(2H)-one (3c)

2-(3-(dimethylamino)propyl)-7-fluoropyrrolo[2,3,4-kl]acridin-1-(2H)-one (3d)

9-methyl-2-(2-(piperidin-1-yl)ethyl) pyrrolo[2,3,4-kl]acridin-1-(2H)-one (4a)

9-chloro-2-(2-(piperidin-1-yl)ethyl) pyrrolo[2,3,4-kl]acridin-1-(2H)-one (4b)

9-methoxy-2-(2-(piperidin-1-yl)ethyl) pyrrolo[2,3,4-kl]acridin-1-(2H)-one (4c)

7-fluoro-2-(2-(piperidin-1-yl)ethyl)pyrrolo[2,3,4-kl]acridin-1-(2H)-one (4d)

2-(2-(dimethylamino)ethyl)-5,9-dimethylpyrrolo[2,3,4-kl]acridin-1-(2H)-one (5a)

9-chloro-2-(2-(dimethylamino)ethyl)-5-methylpyrrolo[2,3,4-kl]acridin-1-(2H)-one (5b)

2-(2-(dimethylamino)ethyl)-9-methoxy-5-methylpyrrolo[2,3,4-kl]acridin-1-(2H)-one (5c)

2-(2-(dimethylamino)ethyl)-9-methoxy-5-methylpyrrolo[2, 3,4-kl]acridin-1-(2H)-one fumarate (5c')

2-(2-(dimethylamino)ethyl)-7-fluoro-5-methylpyrrolo[2,3, 4-kl]acridin-1-(2H)-one (5d)

2-(2-(dimethylamino)ethyl)-5-methylpyrrolo[2,3,4-kl]acridin-1-(2H)-one (5e)

9-bromo-2-(2-(dimethylamino)ethyl)pyrrolo[2,3,4-kl]acridin-1-(2H)-one (7a)

9-bromo-2-(3-(dimethylamino)propyl)pyrrolo[2,3,4-kl]acridin-1-(2H)-one (7b)

2-(2-(dimethylamino)ethyl)-9-iodo-pyrrolo[2,3,4-kl]acridin-1-(2H)-one (7c)

2-(3-(dimethylamino)propyl)-9-iodopyrrolo[2,3,4-kl]acridin-1-(2H)-one (7d)

N-(3-(9-methyl-1-oxopyrrolo[2,3,4-kl]acridin-2-(1H)-yl) propyl)methanesulfonamide (7e)

N-(3-(9-chloro-1-oxopyrrolo[2,3,4-kl]acridin-2-(1H)-yl) propyl)methanesulfonamide (7f)

9-chloro-2-(3-hydroxypropyl)pyrrolo[2,3,4-kl]acridin-1-(2H)-one (7g)

In a second aspect, the present invention provides a process for preparing the fused acridine derivatives, which includes formula (III), formula (IV) reacting with formula (V) to get compounds of formula (I):

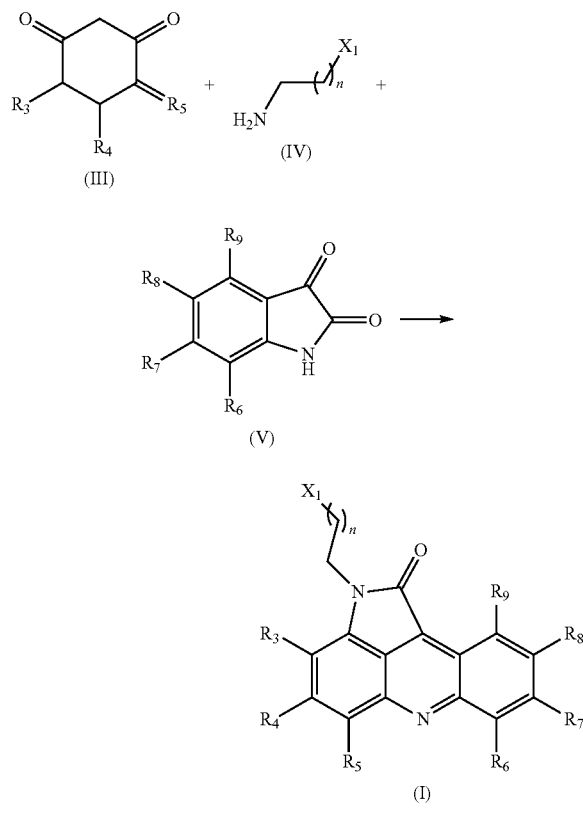

wherein, substituents of $X_1$, $R_3$, $R_4$, $R_5$, $R_6$, $R_7$, $R_8$, and $R_9$, and n in formula (III), (IV), and (V), are defined as those in the formula (I) of this invention.

For the preparing process of the fused acridine derivatives in the present invention, more particularly, two exemplary processes as following can be used:

Process A: To a solution of cyclohexane-1,3-dione derivatives (1.0 mmol) and the side chain with a primary amine (1.0 mmol) in toluene (3 mL) was added an catalytic amount of L-proline (0.1 mmol). The mixture was refluxed for 3-4 hours before the addition of isatin derivatives (1.0 equivalent). The reaction was kept for additional 3-6 hours until the reaction was completed by monitoring with TLC, then evaporated to dryness. The residue was isolated by column chromatography (methylene chloride: methanol=20:1) to furnish the desired products.

Process B: Cyclohexane-1,3-dione derivative (1.3 mmol), amine derivative (1.3 mmol), isatin derivative (1.0 mmol), elemental iodine (1.5 mmol), and acetic acid (4 mL) were added into a reaction tube under an atmospheric pressure of oxygen environment. The reaction mixture was stirred at the rufluxing temperature. After the thin-layer chromatography detection indicated the isatin derivative was completely consumed, the reaction tube was cooled to room temperature, then quenched with a saturated solution of sodium thiosulfate (3 mL). The aqueous solution was extracted with ethyl acetate (3×10 mL). The separated organic phase was dried over anhydrous magnesium sulfate, concentrated, and isolated by column chromatography (methylene chloride: methanol=20:1) to furnish the desired product.

In another aspect of the invention, the present invention provides the use of the above-mentioned fused acridine derivatives as anticancer medicine. An in vitro cell viability assay has showed that compounds of formula (I) of the present invention has significant inhibitory activity against various tumor cell lines, especially in human colon cancer cell HCT116, human prostate cancer cell PC3, human glioma U87MG, human ovarian cancer cell SK-OV-3, human breast cancer MCF-7 and liver cancer cells HepG2.

The present invention also provides a pharmaceutical composition comprising the above-mentioned novel fused acridine derivatives. Content of the active pharmaceutical ingredient in the pharmaceutical composition ranges from 1.0 mg to 500 mg per unit (tablet, capsule, or injection), generally, the total mass quantity of the active pharmaceutical ingredient is of 0.5-95% portion of the total mass quantity of all components. The active pharmaceutical ingredient can be orally administered in the form of solid dosage forms, such as capsules, tablets, powder, or in the form of liquid dosage forms, such as syrup, suspension, also can be administered in the sterile liquid injection dosage forms.

The present invention provides the following drug dosage forms:

Tablet

A large number of tablets can be prepared by conventional process; one unit dosage is as follows: 100 mg of the present invention compound, 0.2 mg talc, 5 mg magnesium stearate, 275 mg of microcrystalline cellulose, 11 mg starch, and 98.8 mg lactose. An appropriate coating may be helpful for oral administration or sustained release of the drug.

Capsule

A large number of capsules can be prepared by filling two pieces of standard hard capsules, each containing 100 mg powder compound of this invention, 175 mg of lactose, 24 mg talc, and 6 mg magnesium stearate.

Injection

A drug injection for parenteral administration can prepared through the following method: after stirring 1.5% (mass) of the present invention compounds, 10% (volume) of propylene glycol, and water, sodium chloride is added into the resulting solution to form an isotonic solution and sterilized.

Better Embodiments of the Present Invention

Embodiments of the present invention will be furtherly described in detail by the following examples. It is understood by a person skilled in the art that the following examples are not intended to limit the scope claimed by the invention in any manner, and modification or equivalence thereof according to the prior art is readily recognized.

$^1$H NMR and $^{13}$C NMR spectra were recorded with Bruker AM-400 MHz spectrometer, wherein $^1$H NMR in 400.00 MHz and $^{13}$C NMR spectra in 100.06 MHz. The chemical shifts were rectified by the signal of TMS in CDCl$_3$. HR-ESI-MS data were measured on Bruker Apex IVFTMS.

The room temperature in the following examples is 25° C.

Example 1

Compound 1a: 2-(2-(dimethylamino)ethyl)pyrrolo[2,3,4-kl]acridin-1-(2H)-one

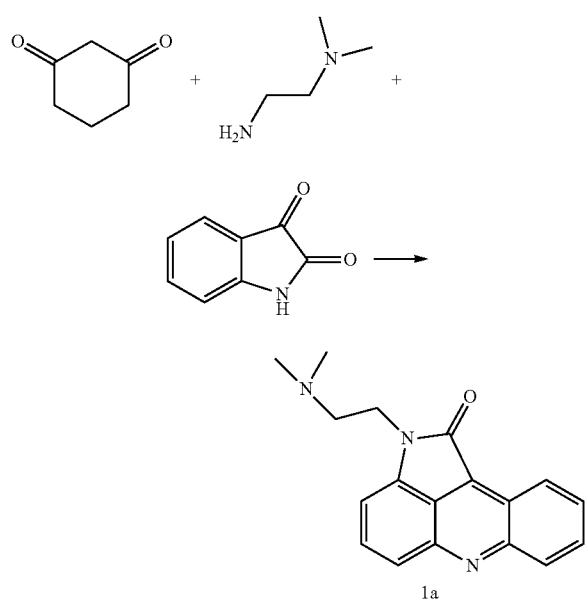

To a solution of cyclohexane-1,3-dione (146 mg, 1.3 mmol) and N$^1$,N$^1$-dimethylethane-1,2-diamine (143 μL, 1.3 mmol) in toluene (5 mL), was added catalytic amount of L-proline (12 mg, 0.1 mmol). The mixture was heated and refluxed for 3-4 hours before isatin (147 mg, 1.0 mmol) was added. The reaction was kept for additional 3-6 hours until the reaction was completed by monitoring with TLC, then the solvent was evaporated to dryness. The residue was isolated by column chromatography (CH$_2$Cl$_2$: MeOH=30:1) to furnish an orange solid (153 mg, yield: 63%). $^1$HNMR (400 MHz, CDCl$_3$) δ=8.83-8.77 (m, 1H), 8.35 (d, J=8.8, 1H), 7.89-7.83 (m, 1H), 7.74 (dd, J=10.8, 5.0, 2H), 7.63 (dd, J=9.0, 6.8, 1H), 6.87 (d, J=6.8, 1H), 4.06 (t, J=7.0, 2H), 2.72 (t, J=7.0, 2H), 2.36 (s, 6H). $^{13}$C NMR (100.6 MHz, CDCl$_3$) δ 167.93, 151.70, 146.26, 140.06, 132.83, 130.65, 130.46, 128.93, 128.06, 124.05, 122.82, 122.09, 119.72, 104.70, 57.44, 45.65, 38.69.

Example 2

Compound 1b: 2-(3-morpholinopropyl)pyrrolo[2,3,4-kl]acridin-1-(2H)-one

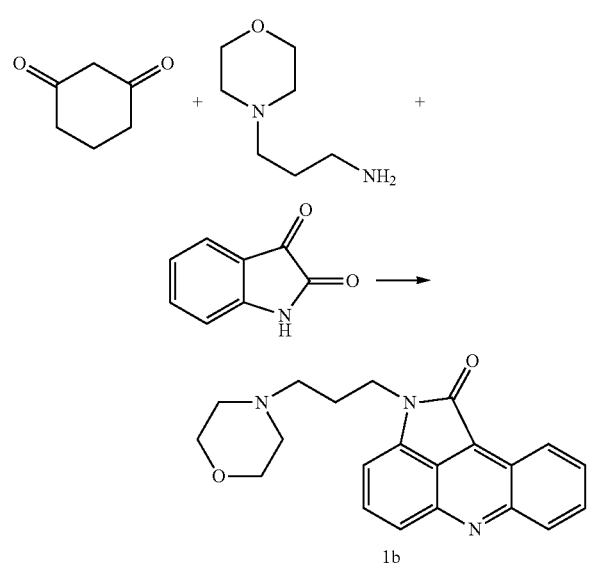

Following the procedure in Example 1, except replace N$^1$,N$^1$-dimethylethane-1,2-diamine with 3-morpholinopropan-1-amine Yield: 51%. $^1$H NMR (400 MHz, CDCl$_3$) δ 8.82-8.76 (m, 1H), 8.36 (d, J=8.8 Hz, 2H), 7.90-7.83 (m, 1H), 7.75 (ddd, J=7.9, 5.8, 1.7 Hz, 2H), 7.62 (dd, J=9.0, 6.8 Hz, 1H), 6.88 (d, J=6.8 Hz, 1H), 4.02 (t, J=6.9 Hz, 2H), 3.70-3.58 (m, 4H), 2.44 (dd, J=15.7, 8.7 Hz, 6H), 2.01 (p, J=6.9 Hz, 2H). $^{13}$C NMR (100.6 MHz, CDCl$_3$) δ 167.97, 151.68, 146.19, 140.28, 132.70, 130.66, 130.45, 128.93, 128.12, 123.98, 122.76, 121.99, 119.59, 104.57, 66.90, 55.82, 53.61, 38.59, 25.51.

Example 3

Compound 1f: 2-(2-(piperidin-1-yl)ethyl)pyrrolo[2,3,4-kl]acridin-1-(2H)-one

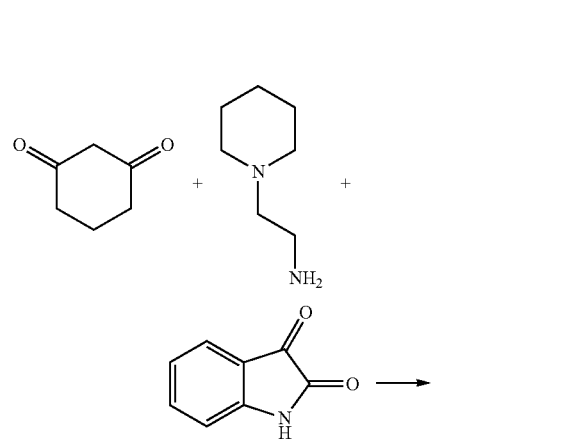

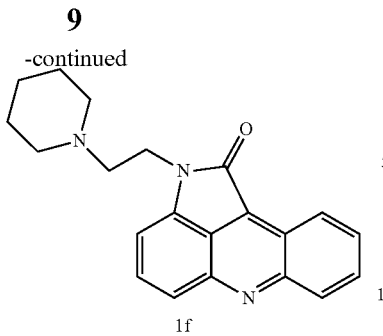

1f

Following the procedure in Example 1, except replace $N^1,N^1$-dimethylethane-1,2-diamine with 2-(piperidin-1-yl)ethan-1-amine. Yield: 56%. $^1$HNMR (400 MHz, CDCl$_3$) δ 8.80 (dd, J=8.5, 0.7 Hz, 1H), 8.35 (d, J=8.8 Hz, 1H), 7.90-7.82 (m, 1H), 7.80-7.68 (m, 2H), 7.67-7.58 (m, 1H), 6.90 (d, J=6.8 Hz, 1H), 4.13-4.03 (m, 2H), 2.77-2.66 (m, 2H), 2.50 (d, J=28.5 Hz, 4H), 1.59 (dt, J=10.9, 5.6 Hz, 4H), 1.45 (dd, J=11.1, 5.8 Hz, 2H). 13C NMR (100.6 MHz, CDCl$_3$) δ 167.84, 151.67, 146.23, 140.20, 132.83, 130.64, 130.42, 128.89, 128.11, 124.05, 122.80, 121.98, 119.70, 104.84, 57.06, 54.83, 38.32, 25.91, 24.20.

Example 4

Compound 1g: 2-(2-(pyrrolidin-1-yl)ethyl)pyrrolo[2,3,4-kl]acridin-1-(2H)-one

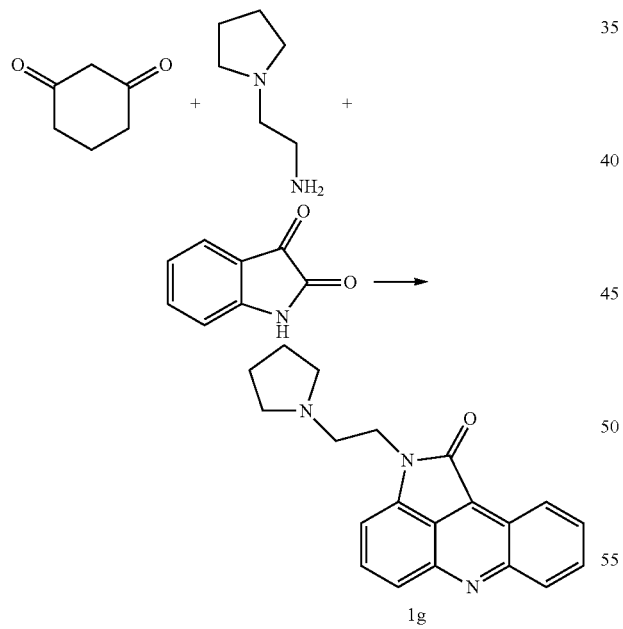

1g

Following the procedure in Example 1, except replace $N^1,N^1$-dimethylethane-1,2-diamine with 2-(pyrrolidin-1-yl)ethan-1-amine. Yield: 60%. $^1$H NMR (400 MHz, CDCl$_3$) δ 8.81 (dd, J=8.5, 0.8 Hz, 1H), 8.36 (d, J=8.8 Hz, 1H), 7.90-7.82 (m, 1H), 7.76 (ddd, J=8.2, 5.2, 1.8 Hz, 2H), 7.65 (dd, J=9.0, 6.8 Hz, 1H), 6.91 (d, J=6.8 Hz, 1H), 4.12 (t, J=7.3 Hz, 2H), 2.96-2.88 (m, 2H), 2.73-2.62 (m, 4H), 1.89-1.74 (m, 4H).

Example 5

Compound 1h: 2-(3-(piperidin-1-yl)propyl)pyrrolo[2,3,4-kl]acridin-1-(2H)-one

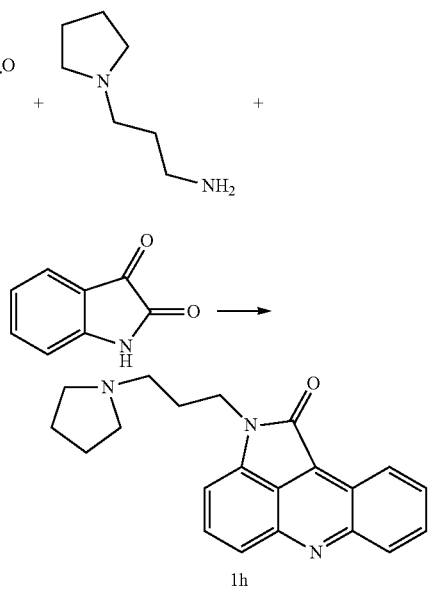

1h

Following the procedure in Example 1, except replace $N^1,N^1$-dimethylethane-1,2-diamine with 3-(pyrrolidin-1-yl)propan-1-amine. Yield: 74%. $^1$H NMR (400 MHz, CDCl$_3$) δ 8.84-8.77 (m, 1H), 8.37 (d, J=8.8 Hz, 1H), 7.93-7.83 (m, 1H), 7.80-7.71 (m, 2H), 7.65 (dd, J=9.0, 6.8 Hz, 1H), 6.93 (d, J=6.8 Hz, 1H), 4.05 (t, J=6.9 Hz, 2H), 2.70-2.53 (m, 6H), 2.15-2.04 (m, 2H), 1.85-1.72 (n, 4H).

Example 6

Compound 2a: 2-(2-(dimethylamino)ethyl)-9-methylpyrrolo[2,3,4-kl]acridin-1-(2H)-one

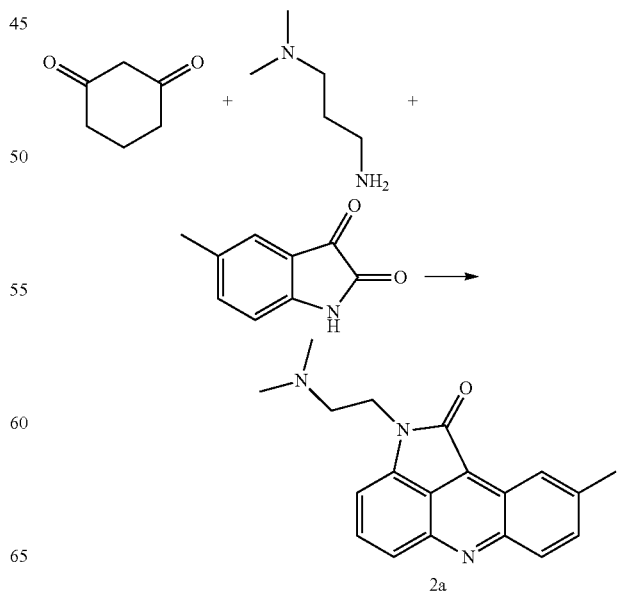

2a

Following the procedure in Example 1, except replace isatin with 5-methyl-isatin. Yield: 45%. ¹H NMR (400 MHz, CDCl₃) δ 8.60 (s, 1H), 8.26 (d, J=9.0 Hz, 1H), 7.78 (d, J=9.0 Hz, 1H), 7.71 (dd, J=9.0, 2.0 Hz, 1H), 7.63 (dd, J=9.0, 6.8 Hz, 1H), 6.90 (d, J=6.8 Hz, 1H), 4.09 (t, J=7.0 Hz, 2H), 2.73 (t, J=7.0 Hz, 2H), 2.65 (s, 3H), 2.36 (s, 6H). 13C NMR (100.6 MHz, CDCl₃) δ 150.77, 145.56, 139.79, 133.32, 132.19, 130.28, 123.10, 122.48, 122.09, 104.62, 57.56, 45.73, 38.78, 22.12. HR-ESI-MS: Calcd. for C₁₉H₂₀N₃O, 306.16009. found: 306.15999 [M+H]⁺.

Example 7

Compound 2b: 9-chloro-2-(2-(dimethylamino)ethyl)pyrrolo[2,3,4-kl]acridin-1-(2H)-one

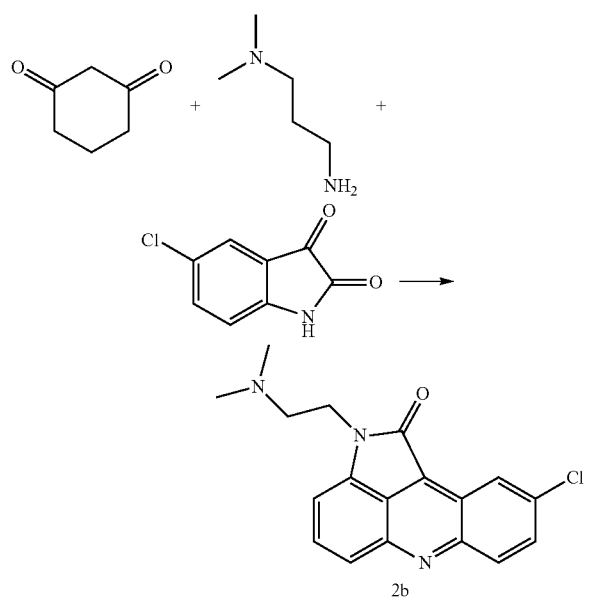

Following the procedure in Example 1, except replace isatin with 5-chloro-isatin. Yield: 44%. ¹H NMR (400 MHz, CDCl₃) δ 8.73 (d, J=2.4 Hz, 1H), 8.24 (d, J=9.3 Hz, 1H), 7.78-7.69 (m, 2H), 7.64 (dd, J=9.0, 6.7 Hz, 1H), 6.90 (d, J=6.7 Hz, 1H), 4.07 (t, J=6.9 Hz, 2H), 2.73 (t, J=6.9 Hz, 2H), 2.36 (s, 6H). ¹³C NMR (100.6 MHz, CDCl₃) δ 167.43, 149.80, 139.98, 135.49, 133.12, 132.02, 131.72, 127.21, 122.71, 122.04, 119.92, 105.27, 57.47, 45.68, 38.79. HR-ESI-MS: Calcd. for C₁₈H₁₇ClN₃O [M+H]⁺ 326.10547. found: 326.10584.

Example 8

Compound 2c: 2-(2-(dimethylamino)ethyl)-9-methoxypyrrolo[2,3,4-kl]acridin-1-(2H)-one

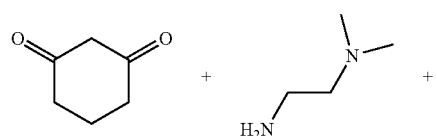

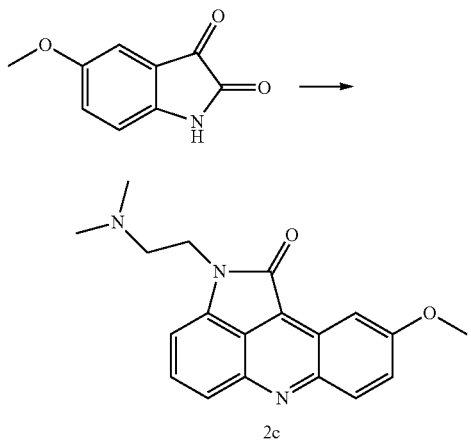

Following the procedure in Example 1, except replace isatin with 5-methoxyl-isatin. Yield: 51%. ¹HNMR (400 MHz, CDCl₃) δ 8.23 (d, J=9.5 Hz, 1H), 8.01 (d, J=2.8 Hz, 1H), 7.78 (d, J=8.9 Hz, 1H), 7.61 (dd, J=8.9, 6.9 Hz, 1H), 7.52 (dd, J=9.5, 2.9 Hz, 1H), 6.92 (d, J=6.8 Hz, 1H), 4.09 (t, J=7.0 Hz, 2H), 4.05 (s, 3H), 2.73 (t, J=7.0 Hz, 2H), 2.37 (s, 6H). ¹³CNMR (100.6 MHz, CDCl₃) δ 168.31, 160.16, 148.97, 144.02 (2C), 139.45, 132.18, 131.22, 125.58, 124.71, 122.02, 119.65, 104.88, 99.88, 57.60, 55.99, 45.75, 38.78. HR-ESI-MS: Calcd for C₁₉H₂₀N₃O₂ [M+H]⁺ 322.15500. found: 322.15482.

Example 9

Compound 2d: 2-(2-(dimethylamino)ethyl)-7-fluoropyrrolo[2,3,4-kl]acridin-1-(2H)-one

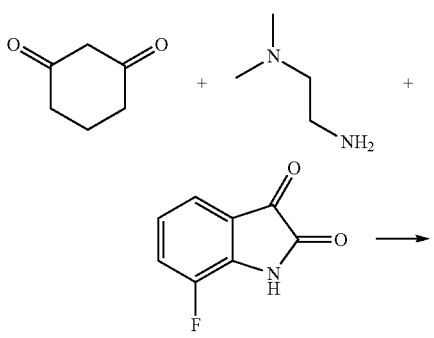

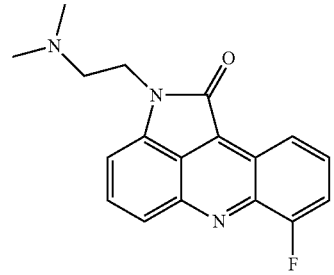

Following the procedure in Example 1, except replace isatin with 7-fluoro-isatin. Yield: 88%. ¹H NMR (400 MHz, CDCl$_3$) δ 8.59 (d, J=8.5 Hz, 1H), 7.85 (d, J=9.0 Hz, 1H), 7.75-7.65 (m, 2H), 7.56 (ddd, J=11.0, 7.6, 1.1 Hz, 1H), 6.92 (d, J=6.8 Hz, 1H), 4.07 (t, J=6.9 Hz, 2H), 2.73 (t, J=6.9 Hz, 2H), 2.36 (s, 6H). $^{13}$C NMR (100.6 MHz, CDCl$_3$) δ 167.56, 159.52, 156.94, 146.04, 142.37, 140.01, 133.42, 128.58, 128.21, 123.84, 122.43, 120.22-119.93, 113.78, 105.35, 57.47, 45.69, 38.84. HR-ESI-MS: Calcd for C$_{18}$H$_{17}$FN$_3$O [M+H]$^+$ 310.13502. found: 310.13437.

Example 10

Compound 2e: 2-(2-(dimethylamino)propyl)-5-nitropyrrolo[2,3,4-kl]acridin-1-(2H)-one

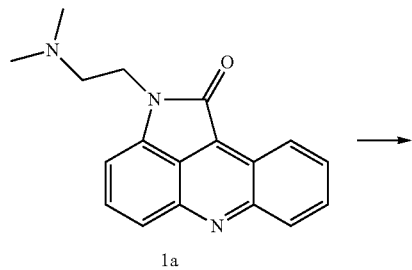

1a

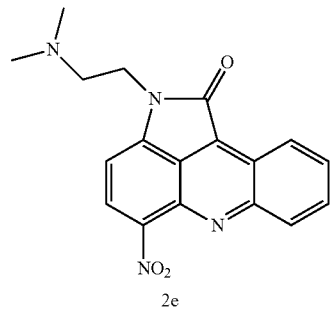

2e

Compound 1a (53 mg, 0.18 mmol) was dissolved in acetic acid (1 mL), and dissolved completely before 65% HNO$_3$ (40 μL) was slowly added. Nitration reaction was carried on in refluxing system. After the reaction was completed, the reaction mixture was quenched with adequate solid NaHCO$_3$, then extracted with CH$_2$Cl$_2$ (2×5 mL). The organic phase was separated and concentrated. The residue was purified on column chromatography (CH$_2$Cl$_2$:MeOH=20:1) to furnish title product (24 mg) in 40% yield. $^1$H NMR (400 MHz, CDCl$_3$) δ 8.82 (d, J=8.4 Hz, 1H), 8.63 (d, J=7.7 Hz, 1H), 8.52 (d, J=8.9 Hz, 1H), 8.04-7.93 (m, 1H), 7.91-7.81 (m, 1H), 6.96 (d, J=7.7 Hz, 1H), 4.10 (t, J=6.6 Hz, 2H), 2.73 (t, J=6.6 Hz, 2H), 2.35 (s, 6H). $^{13}$C NMR (100.6 MHz, CDCl$_3$) δ 168.27, 153.64, 145.93, 140.05, 138.21, 133.02, 131.95, 131.73, 130.76, 127.98, 123.85, 122.65, 119.44, 102.33, 57.50, 45.71, 39.06. HR-ESI-MS: Calcd for C$_{18}$H$_{17}$N$_4$O$_3$ [M+H]$^+$ 337.12952. found: 337.12941.

Example 11

Compound 3a: 2-(3-(dimethylamino)propyl)-9-methylpyrrolo[2,3,4-kl]acridin-1-(2H)-one

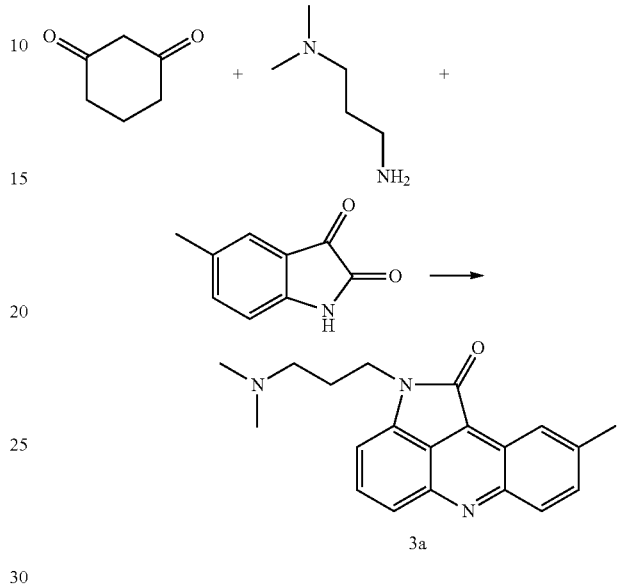

3a

Following the procedure in Example 1, except replace isatin with 5-methyl-isatin, and replace N$^1$,N$^1$-dimethylethane-1,2-diamine with N$^1$,N$^1$-dimethylpropane-1,3-diamine. Yield: 74%. $^1$H NMR (400 MHz, CDCl$_3$) δ 8.57 (s, 1H), 8.25 (d, J=8.9 Hz, 1H), 7.75 (d, J=8.9 Hz, 1H), 7.70 (d, J=9.0 Hz, 1H), 7.62 (t, J=7.9 Hz, 1H), 6.91 (d, J=6.7 Hz, 1H), 4.02 (t, J=7.0 Hz, 2H), 2.64 (s, 3H), 2.41 (t, J=7.1 Hz, 2H), 2.25 (s, 6H), 2.01 (dd, J=14.1, 7.0 Hz, 2H). 13C NMR (100.6 MHz, CDCl$_3$) δ 168.18, 150.71, 145.50, 140.12, 139.75, 133.28, 132.21, 130.25, 123.03, 122.43, 121.98, 119.63, 104.69, 56.68, 45.39, 38.55, 26.97, 22.11. HR-ESI-MS: Calcd for C$_{20}$H$_{22}$N$_3$O [M+H]$^+$ 320.17574. found: 320.17539.

Example 12

Compound 3b: 9-chloro-2-(3-(dimethylamino)propyl)pyrrolo[2,3,4-kl]acridin-1-(2H)-one

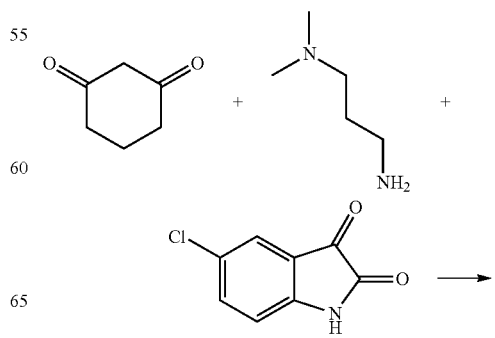

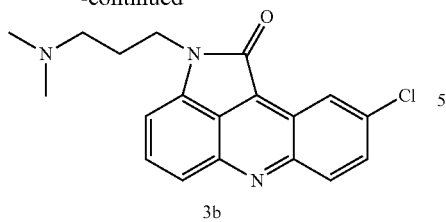

3b

Following the procedure in Example 1, except replace isatin with 5-chloro-isatin, and replace N¹,N¹-dimethylethane-1,2-diamine with N¹,N¹-dimethylpropane-1,3-diamine. Yield: 62%. ¹H NMR (400 MHz, CDCl$_3$) δ 8.79 (d, J=2.3 Hz, 1H), 8.29 (d, J=9.3 Hz, 1H), 7.83-7.71 (m, 2H), 7.67 (dd, J=9.0, 6.8 Hz, 1H), 6.96 (d, J=6.7 Hz, 1H), 4.03 (t, J=7.0 Hz, 2H), 2.41 (t, J=7.1 Hz, 2H), 2.25 (s, 6H), 2.06-1.96 (m, 2H). ¹³C NMR (100.6 MHz, CDCl$_3$) δ 167.55, 149.91, 146.34, 140.24, 135.53, 133.19, 132.09, 131.77, 127.38, 122.79 (2C), 122.04, 119.94, 105.37, 56.61, 45.40, 38.64, 26.93. HR-ESI-MS: Calcd for $C_{19}H_{19}ClN_3O$ [M+H]$^+$ 340.12112, found: 340.12121.

Example 13

Compound 3c: 2-(3-(dimethylamino)propyl)-9-methoxypyrrolo[2,3,4-kl]acridin-1-(2H)-one

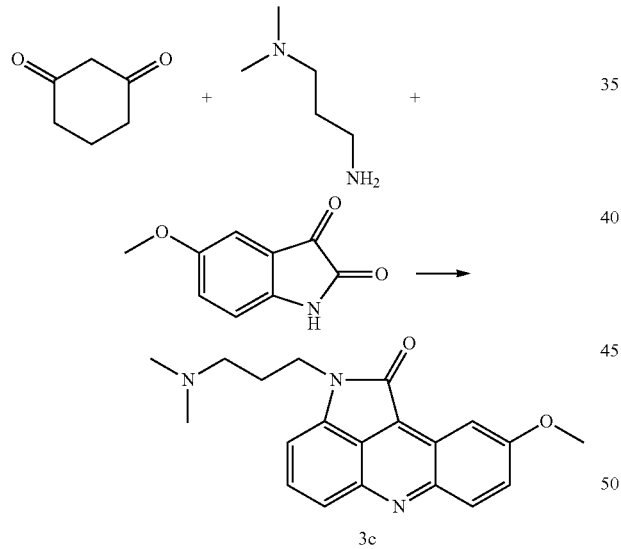

3c

Following the procedure in Example 1, except replace isatin with 5-methoxyl-isatin, and replace N¹,N¹-dimethylethane-1,2-diamine with N¹,N¹-dimethylpropane-1,3-diamine. Yield: 66%. ¹H NMR (400 MHz, CDCl$_3$) δ 8.23 (d, J=9.5 Hz, 1H), 8.01 (d, J=2.8 Hz, 1H), 7.77 (d, J=8.9 Hz, 1H), 7.61 (dd, J=8.9, 6.9 Hz, 1H), 7.52 (dd, J=9.5, 2.9 Hz, 1H), 6.95 (d, J=6.8 Hz, 1H), 4.05 (s, 3H), 4.03 (d, J=7.0 Hz, 2H), 2.41 (t, J=7.1 Hz, 2H), 2.25 (s, 6H), 2.11-1.95 (n, 2H). ¹³C NMR (100.6 MHz, CDCl$_3$) δ 168.35, 160.15, 148.95, 144.00, 139.62, 132.17, 131.27, 125.59 (2C), 124.68, 121.94, 119.55, 105.00, 99.86, 56.71, 55.99, 45.41, 38.58, 27.01. HR-ESI-MS: Calcd for $C_{20}H_{22}N_3O_2$ [M+H]$^+$ 336.17065. found: 336.17093.

Example 14

Compound 3d: 2-(3-(dimethylamino)propyl)-7-fluoropyrrolo[2,3,4-kl]acridin-1-(2H)-one

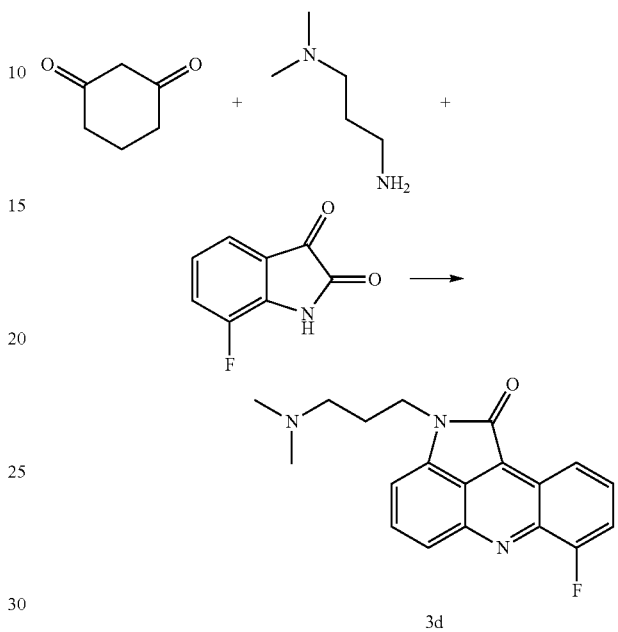

3d

Following the procedure in Example 1, except replace isatin with 7-fluoro-isatin, and replace N¹,N¹-dimethylethane-1,2-diamine with N¹,N¹-dimethylpropane-1,3-diamine. Yield: 88%. ¹H NMR (400 MHz, CDCl$_3$) δ 8.51 (d, J=8.5 Hz, 1H), 7.78 (d, J=9.0 Hz, 1H), 7.72-7.60 (m, 2H), 7.57-7.50 (m, 1H), 6.91 (d, J=6.8 Hz, 1H), 3.99 (t, J=7.0 Hz, 2H), 2.39 (t, J=7.0 Hz, 2H), 2.24 (s, 6H), 2.06-1.92 (m, 2H). 13C NMR (100.6 MHz, CDCl$_3$) δ 167.41, 159.42, 156.84, 145.86, 142.20, 140.08, 133.37, 128.46, 128.04, 123.64, 122.23, 119.90, 113.67, 105.31, 56.55, 45.37, 38.57, 26.86. HR-ESI-MS: Calcd for $C_{19}H_{19}FN_3O$ [M+H]$^+$ 324.15067, found: 324.15099.

Example 15

Compound 4a: 9-methyl-2-(2-(piperidin-1-yl)ethyl)pyrrolo[2,3,4-kl]acridin-1-(2H)-one

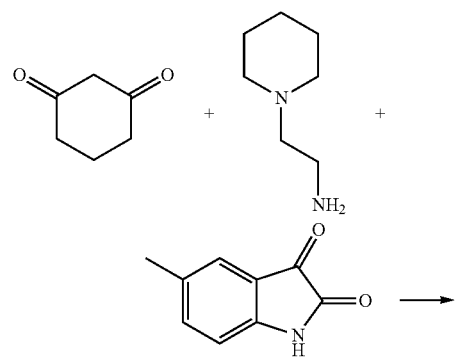

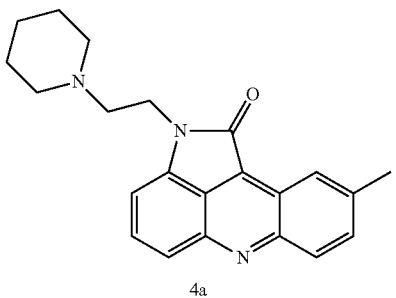

4a

Following the procedure in Example 1, except replace isatin with 5-methyl-isatin, and replace N¹,N¹-dimethyl-ethane-1,2-diamine with 2-(piperidin-1-yl)ethan-1-amine. Yield: 66%. ¹H NMR (400 MHz, CDCl$_3$) δ 8.57 (s, 1H), 8.24 (d, J=9.0 Hz, 1H), 7.75 (d, J=9.0 Hz, 1H), 7.69 (dd, J=9.0, 2.0 Hz, 1H), 7.62 (dd, J=9.0, 6.8 Hz, 1H), 6.90 (d, J=6.8 Hz, 1H), 4.14-4.05 (m, 2H), 2.76-2.69 (m, 2H), 2.64 (s, 3H), 2.56 (d, J=15.7 Hz, 4H), 1.59 (dt, J=11.0, 5.6 Hz, 4H), 1.45 (dd, J=11.2, 5.9 Hz, 2H). 13C NMR (100.6 MHz, CDCl$_3$) δ 168.05, 150.68, 145.49, 140.05, 139.75, 133.28, 132.20, 130.22, 126.95, 123.04, 122.44, 121.96, 119.71, 104.78, 57.08, 54.83, 38.32, 25.93, 24.22, 22.11. HR-ESI-MS: Calcd for $C_{22}H_{24}N_3O$ [M+H]⁺ 346.19139. found: 346.19159.

Example 16

Compound 4b: 9-chloro-2-(2-(piperidin-1-yl)ethyl)pyrrolo[2,3,4-kl]acridin-1-(2H)-one

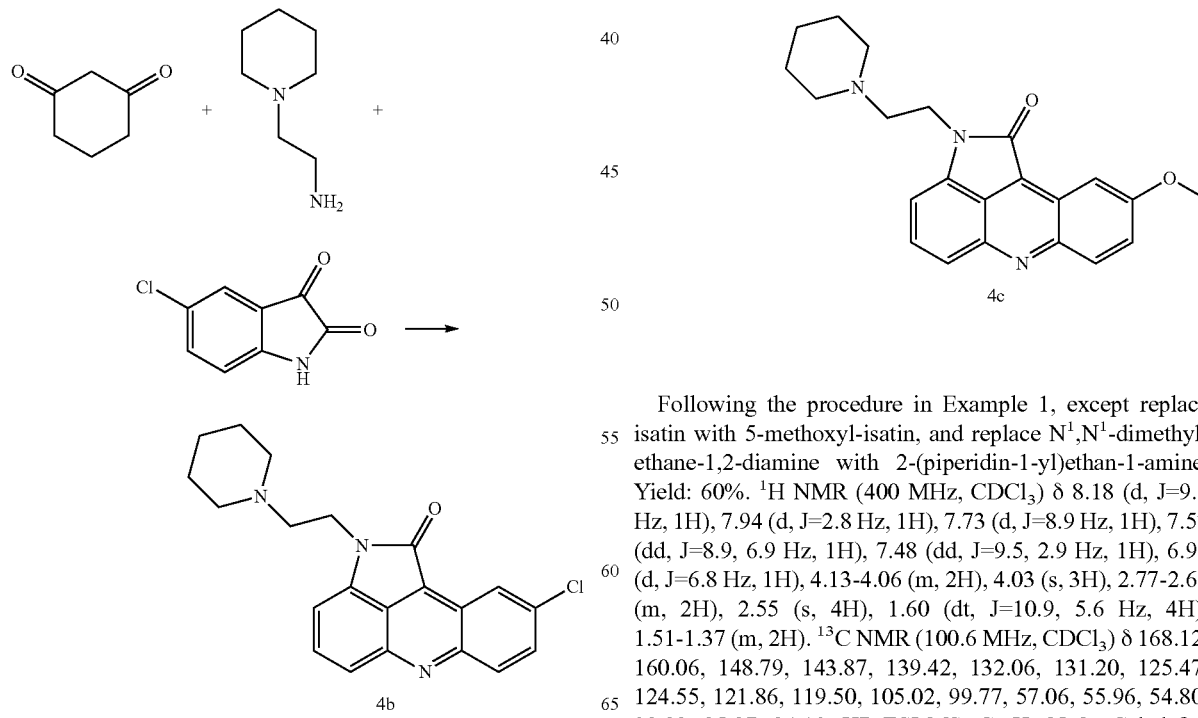

4b

Following the procedure in Example 1, except replace isatin with 5-chloro-isatin, and replace N¹,N¹-dimethyl-ethane-1,2-diamine with 2-(piperidin-1-yl)ethan-1-amine. Yield: 46%. ¹H NMR (400 MHz, CDCl$_3$) δ 8.82 (d, J=2.4 Hz, 1H), 8.31 (d, J=9.3 Hz, 1H), 7.84-7.74 (m, 2H), 7.68 (dd, J=9.0, 6.8 Hz, 1H), 6.96 (d, J=6.8 Hz, 1H), 4.10 (t, J=7.1 Hz, 2H), 2.73 (t, J=7.1 Hz, 2H), 2.53 (s, 4H), 1.58 (dt, J=11.0, 5.6 Hz, 4H), 1.50-1.40 (m, 2H). ¹³C NMR (100.6 MHz, CDCl$_3$) δ 167.54, 149.93, 146.40, 139.95, 135.52, 133.19, 132.10, 131.80, 127.34, 122.90, 122.80, 122.03, 120.09, 105.49, 57.09, 54.87, 38.48, 25.96, 24.23. HR-ESI-MS: Calcd for $C_{21}H_{21}ClN_3O$ [M+H]⁺ 366.13677. found: 366.13755.

Example 17

Compound 4c: 9-methoxy-2-(2-(piperidin-1-yl)ethyl)pyrrolo[2,3,4-kl]acridin-1-(2H)-one

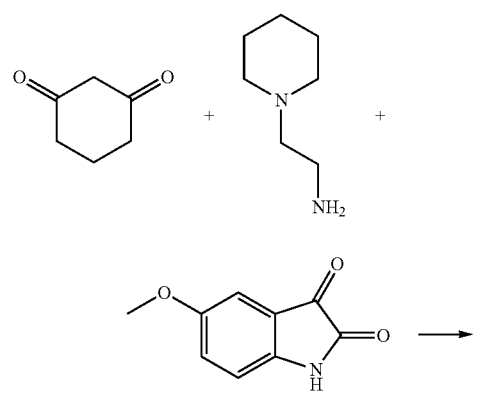

4c

Following the procedure in Example 1, except replace isatin with 5-methoxyl-isatin, and replace N¹,N¹-dimethyl-ethane-1,2-diamine with 2-(piperidin-1-yl)ethan-1-amine. Yield: 60%. ¹H NMR (400 MHz, CDCl$_3$) δ 8.18 (d, J=9.5 Hz, 1H), 7.94 (d, J=2.8 Hz, 1H), 7.73 (d, J=8.9 Hz, 1H), 7.57 (dd, J=8.9, 6.9 Hz, 1H), 7.48 (dd, J=9.5, 2.9 Hz, 1H), 6.91 (d, J=6.8 Hz, 1H), 4.13-4.06 (m, 2H), 4.03 (s, 3H), 2.77-2.69 (m, 2H), 2.55 (s, 4H), 1.60 (dt, J=10.9, 5.6 Hz, 4H), 1.51-1.37 (m, 2H). ¹³C NMR (100.6 MHz, CDCl$_3$) δ 168.12, 160.06, 148.79, 143.87, 139.42, 132.06, 131.20, 125.47, 124.55, 121.86, 119.50, 105.02, 99.77, 57.06, 55.96, 54.80, 38.22, 25.87, 24.19. HR-ESI-MS: $C_{22}H_{24}N_3O_2$ Calcd for, 362.18630 [M+H]⁺. found: 362.18646 [M+H]⁺.

Example 18

Compound 4d: 7-fluoro-2-(2-(piperidin-1-yl)ethyl)pyrrolo[2,3,4-kl]acridin-1-(2H)-one

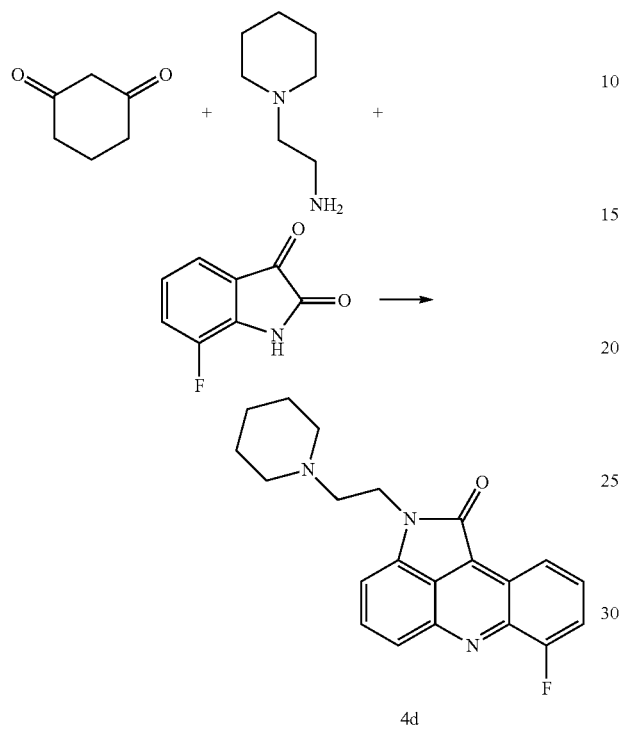

4d

Following the procedure in Example 1, except replace N¹,N¹-dimethylethane-1,2-diamine with 2-(piperidin-1-yl)ethan-1-amine, and replace isatin with 7-fluoro-isatin. Yield: 90%. ¹H NMR (400 MHz, CDCl₃) δ 8.52 (d, J=8.4 Hz, 1H), 7.78 (d, J=9.0 Hz, 1H), 7.65 (ddd, J=14.0, 8.4, 6.0 Hz, 2H), 7.53 (ddd, J=10.9, 7.6, 1.0 Hz, 1H), 6.89 (d, J=6.8 Hz, 1H), 4.05 (t, J=7.1 Hz, 2H), 2.71 (t, J=7.1 Hz, 2H), 2.53 (s, 4H), 1.58 (dt, J=10.9, 5.6 Hz, 4H), 1.50-1.34 (m, 2H). ¹³C NMR (100.6 MHz, CDCl₃) δ 167.31, 159.43, 156.85, 145.86, 142.19, 140.01, 133.36, 128.47, 128.02, 123.66, 122.23, 119.95, 113.68, 105.43, 57.00, 54.80, 38.35, 25.89, 24.19. HR-ESI-MS: Calcd for $C_{21}H_{21}FN_3O$ [M+H]⁺ 350.16632. found: 350.16657.

Example 19

Compound 5a: 2-(2-(dimethylamino)ethyl)-5,9-dimethylpyrrolo[2,3,4-kl]-acridin-1-(2H)-one

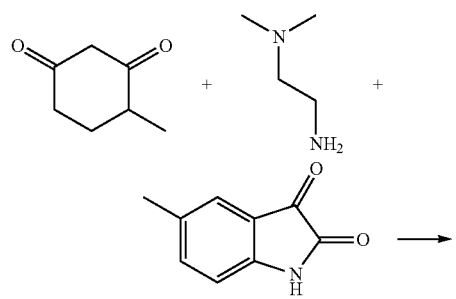

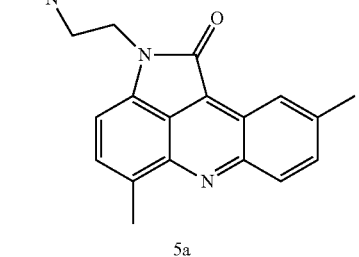

5a

Following the procedure in Example 1, except replace isatin with 5-methyl-isatin, and replace cyclohexane-1,3-dione with 4-methyl-cyclohexane-1,3-dione. Yield: 24%. ¹H NMR (400 MHz, CDCl₃) δ 8.62 (s, 1H), 8.31 (d, J=9.0 Hz, 1H), 7.70 (dd, J=9.0, 2.0 Hz, 1H), 7.39 (dd, J=6.9, 1.2 Hz, 1H), 6.81 (d, J=6.9 Hz, 1H), 4.08 (t, J=7.0 Hz, 2H), 2.83 (d, J=0.9 Hz, 3H), 2.74 (t, J=7.0 Hz, 2H), 2.64 (s, 3H), 2.37 (s, 6H). HR-ESI-MS: Calcd for $C_{20}H_{22}N_3O$ [M+H]⁺ 320.17574. found: 320.17571.

Example 20

Compound 5b: 9-chloro-2-(2-(dimethylamino)ethyl)-5-methylpyrrolo[2,3,4-kl]-acridin-1-(2H)-one

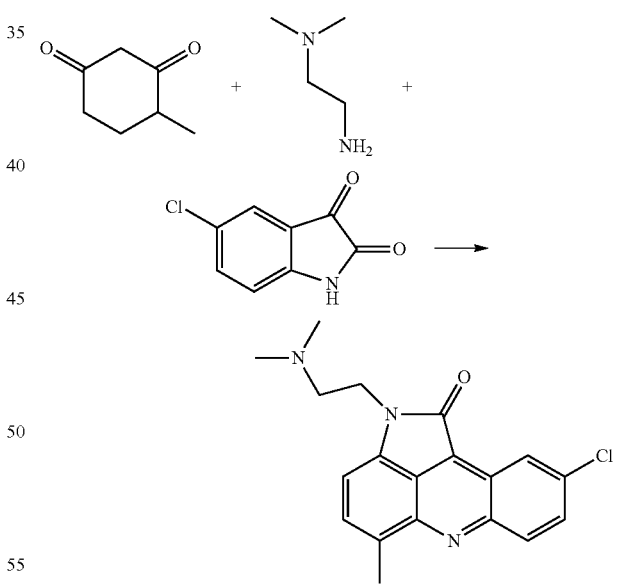

5b

Following the procedure in Example 1, except replace isatin with 5-chloro-isatin, and replace cyclohexane-1,3-dione with 4-methyl-cyclohexane-1,3-dione. Yield: 25%. ¹H NMR (400 MHz, CDCl₃) δ 8.78 (d, J=2.3 Hz, 1H), 8.33 (d, J=9.3 Hz, 1H), 7.77 (dd, J=9.3, 2.4 Hz, 1H), 7.41 (dd, J=6.9, 1.2 Hz, 1H), 6.83 (d, J=6.9 Hz, 1H), 4.08 (t, J=6.8 Hz, 2H), 2.82-2.70 (m, 5H), 2.38 (s, 6H). HR-ESI-MS: Calcd for $C_{19}H_{19}ClN_3O$ [M+H]⁺ 340.12112. found: 340.12111.

Example 21

Compound 5c: 2-(2-(dimethylamino)ethyl)-9-methoxy-5-methylpyrrolo[2,3,4-kl]-acridin-1-(2H)-one

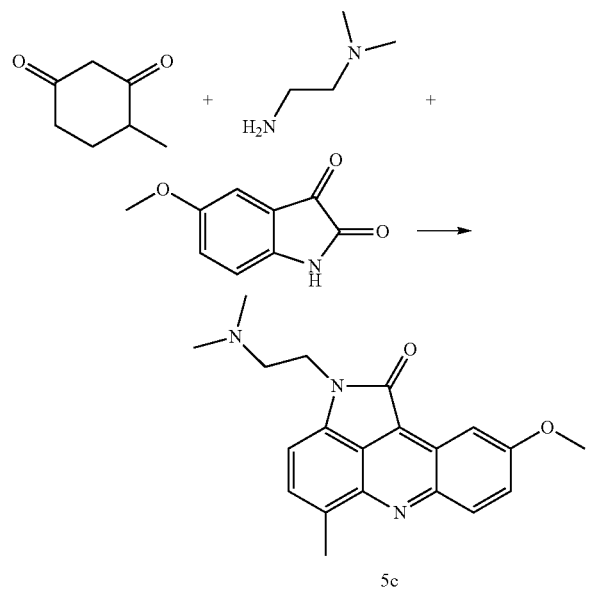

5c

Following the procedure in Example 1, except replace isatin with 5-methoxyl-isatin, and replace cyclohexane-1,3-dione with 4-methyl-cyclohexane-1,3-dione. Yield: 50%. $^1$H NMR (400 MHz, CDCl$_3$) δ 8.29 (d, J=9.5 Hz, 1H), 8.05 (d, J=2.8 Hz, 1H), 7.51 (dd, J=9.5, 2.9 Hz, 1H), 7.37 (dd, J=6.9, 1.0 Hz, 1H), 6.83 (d, J=6.9 Hz, 1H), 4.09 (t, J=7.1 Hz, 2H), 4.05 (s, 3H), 2.83 (s, 3H), 2.74 (t, J=7.1 Hz, 2H), 2.38 (s, 6H). $^{13}$C NMR (100.6 MHz, CDCl$_3$) δ168.39, 160.20, 148.44, 144.05, 137.42, 132.51, 132.08, 131.17, 129.49, 125.05, 124.54, 119.60, 105.33, 99.85, 57.58, 55.95, 45.69, 38.65, 16.17. HR-ESI-MS: Calcd for C$_{20}$H$_{22}$N$_3$O$_2$ [M+H]$^+$ 336.17065. found: 336.17096.

Example 22

Compound 5d: 2-(2-(dimethylamino)ethyl)-7-fluoro-5-methylpyrrolo[2,3,4-kl]-acridin-1-(2H)-one

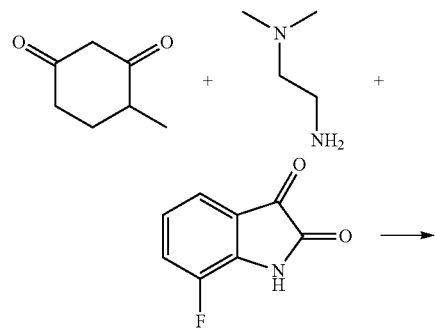

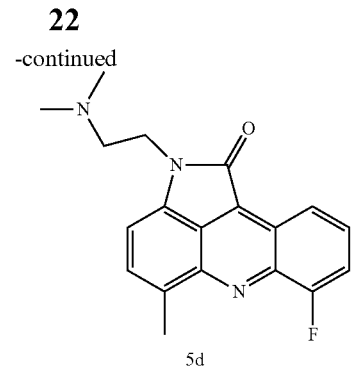

5d

Following the procedure in Example 1, except replace isatin with 7-fluoro-isatin, and replace cyclohexane-1,3-dione with 4-methyl-cyclohexane-1,3-dione. Yield: 24%. $^1$H NMR (400 MHz, CDCl$_3$) δ 8.55 (d, J=8.5 Hz, 1H), 7.64 (td, J=8.0, 5.0 Hz, 1H), 7.55-7.46 (m, 1H), 7.35 (dd, J=6.9, 1.0 Hz, 1H), 6.77 (d, J=6.9 Hz, 1H), 4.05 (t, J=7.0 Hz, 2H), 2.80-2.70 (m, 5H), 2.37 (s, 6H). $^{13}$C NMR (100.6 MHz, CDCl$_3$) δ 167.56, 159.75, 157.16, 145.88, 137.77, 131.60, 131.37, 128.37, 128.10, 123.66, 120.13, 119.87, 113.39, 105.86, 57.32, 45.46, 38.48, 16.01. HR-ESI-MS: Calcd for C$_{19}$H$_{19}$FN$_3$O [M+H]$^+$ 324.15067. found: 324.15127.

Example 23

Compound 5e: 2-(2-(dimethylamino)ethyl)-5-methylpyrrolo[2,3,4-kl]-acridin-1-(2H)-one

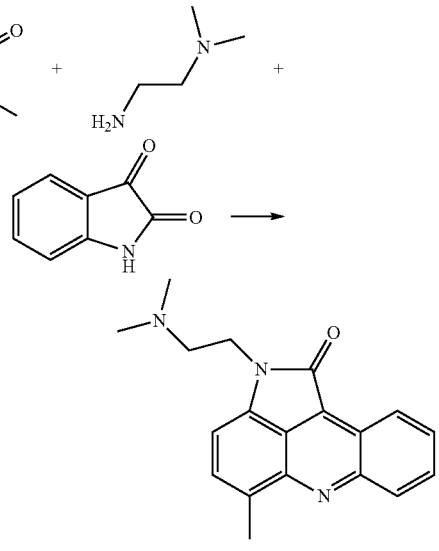

5e

Following the procedure in Example 1, except replace cyclohexane-1,3-dione with 4-methyl-cyclohexane-1,3-dione. Yield: 40%. $^1$HNMR (400 MHz, CDCl$_3$) δ 8.76 (d, J=8.4 Hz, 1H), 8.35 (d, J=8.7 Hz, 1H), 7.85-7.65 (m, 2H), 7.33-7.25 (m, 1H), 6.70 (d, J=6.9 Hz, 1H), 4.02 (t, J=7.0 Hz, 2H), 2.76 (s, 3H), 2.71 (t, J=7.0 Hz, 2H), 2.35 (s, 6H). $^{13}$C NMR (100.6 MHz, CDCl$_3$) δ 167.91, 151.02, 146.19, 137.93, 131.17, 130.83 (2C), 129.92, 128.67, 128.07, 123.89, 122.61, 119.78, 105.04, 57.49, 45.63, 38.58, 16.14. HR-ESI-MS: Calcd for C$_{19}$H$_{20}$N$_3$O [M+H]$^+$ 306.16009. found: 306.15977.

Example 24

Compound 5c': 2-(2-(dimethylamino)ethyl)-9-methoxy-5-methylpyrrolo[2,3,4-kl]-acridin-1-(2H)-one fumarate

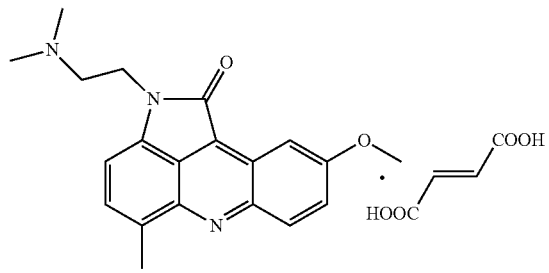

A suspension of 2-(2-(dimethylamino)ethyl)-9-methoxy-5-methyl pyrrolo[2,3,4-kl]-acridin-1-(2H)-one (5c) in a suitable amount of methanol was heated to reflux before it became clear. Fumaric acid (1.2 eq.) was added to the above solution, cooled, until a precipitate formed. 2-(2-(dimethylamino)ethyl)-9-methoxy-5-methyl pyrrolo[2,3,4-kl]-acridin-1-(2H)-one fumarate (5c') was collected in 75% yield after suction filtration and dryness. $^1$H NMR (400 MHz, DMSO) δ 8.24 (d, J=9.5 Hz, 1H), 7.88 (d, J=2.6 Hz, 1H), 7.59 (dd, J=9.5, 2.7 Hz, 1H), 7.47 (d, J=6.9 Hz, 1H), 7.12 (d, J=6.9 Hz, 1H), 6.55 (s, 2H), 4.08 (t, J=6.3 Hz, 2H), 4.01 (s, 3H), 2.83 (t, J=6.3 Hz, 2H), 2.71 (s, 3H), 2.37 (s, 6H).

Example 25

Compound 3b': 9-chloro-2-(3-(dimethylamino)propyl)pyrrolo[2,3,4-kl]acridin-1-(2H)-one fumarate

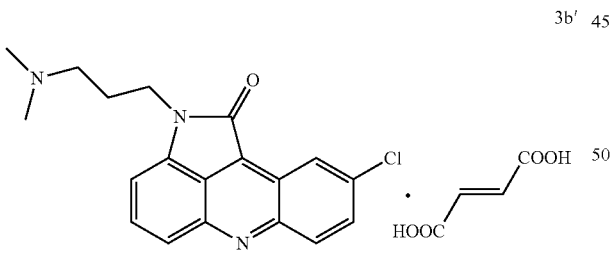

A suspension of 9-chloro-2-(3-(dimethylamino)propyl)pyrrolo[2,3,4-kl]acridin-1-(2H)-one (3b) in a suitable amount of methanol was heated to reflux before it became clear. Fumaric acid (1.2 eq.) was added to the above solution and refluxed for 30-60 minutes, cooled, until a precipitate formed. 9-chloro-2-(3-(dimethylamino)propyl)pyrrolo[2,3,4-kl]acridin-1-(2H)-one fumarate was collected in 74% yield after suction filtration and dryness. 1H NMR (400 MHz, DMSO) δ 8.53 (s, 1H), 8.33 (d, J=9.3 Hz, 1H), 7.95 (d, J=9.3 Hz, 1H), 7.85-7.63 (m, 2H), 7.25 (d, J=6.6 Hz, 1H), 6.54 (s, 2H), 3.98 (t, J=6.7 Hz, 2H), 2.76 (m, 2H), 2.43 (s, 6H), 2.11-1.94 (m, 2H).

Example 26

Compound 7a: 9-bromo-2-(2-(dimethylamino)ethyl)pyrrolo[2,3,4-kl]acridin-1-(2H)-one

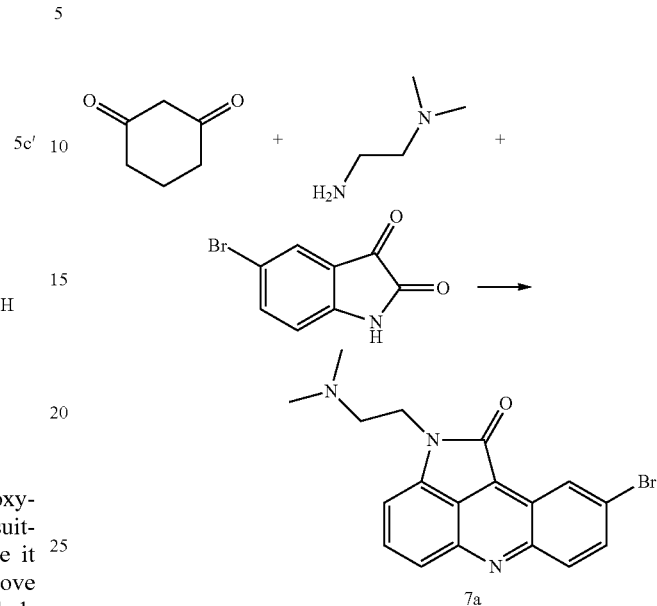

Following the procedure in Example 1, except replace isatin with 5-bromo-isatin. Yield: 24%. $^1$H NMR (400 MHz, CDCl$_3$) δ 8.93 (d, J=2.2 Hz, 1H), 8.17 (d, J=9.3 Hz, 1H), 7.92-7.83 (m, 1H), 7.78-7.60 (m, 2H), 6.90 (d, J=6.6 Hz, 1H), 4.11-4.01 (m, 2H), 2.76-2.68 (m, 2H), 2.36 (d, J=3.3 Hz, 6H). $^{13}$C NMR (100.6 MHz, CDCl$_3$) δ 167.43, 149.94, 146.37, 140.04, 134.15, 133.20, 132.03, 127.07, 126.18, 124.08, 123.15, 122.07, 119.91, 105.29, 57.48, 45.69, 38.81.

Example 27

Compound 7b: 9-bromo-2-(3-(dimethylamino)propyl)pyrrolo[2,3,4-kl]acridin-1-(2H)-one

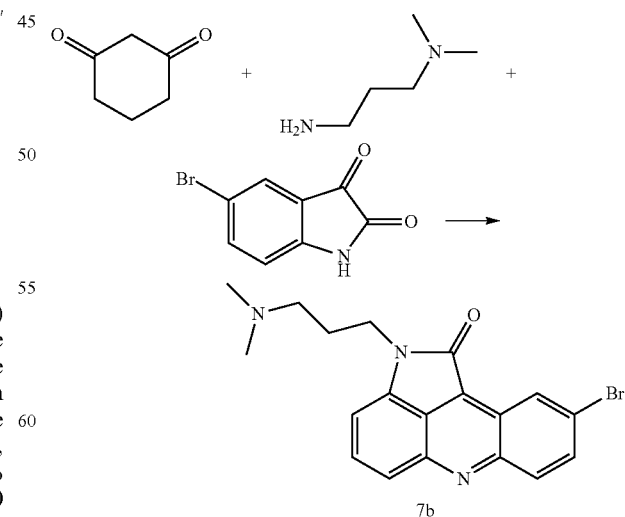

Following the procedure in Example 1, except replace isatin with 5-bromo-isatin, and replace N$^1$,N$^1$-dimethylethane-1,2-diamine with $N^1,N^1$-dimethylpropane-1,3-diamine. Yield: 32%. $^1$H NMR (400 MHz, CDCl$_3$) δ 8.88 (dd, J=8.1, 2.1 Hz, 1H), 8.14 (d, J=9.3 Hz, 1H), 7.86 (dt, J=10.2, 5.1 Hz, 1H), 7.73-7.56 (m, 2H), 6.92 (t, J=6.2 Hz, 1H), 4.00 (t, J=7.0 Hz, 2H), 2.41 (t, J=7.1 Hz, 2H), 2.25 (s, 6H), 1.99 (t, J=7.0 Hz, 2H). $^{13}$C NMR (100.6 MHz, CDCl$_3$) δ 167.44, 149.90, 146.33, 140.18, 134.11, 133.23, 132.02, 127.06, 126.12, 124.05, 123.09, 122.00, 119.77, 105.36, 56.57, 45.35, 38.61, 26.88.

Example 28

Compound 7c: 2-(2-(dimethylamino)ethyl)-9-iodopyrrolo[2,3,4-kl]acridin-1-(2H)-one

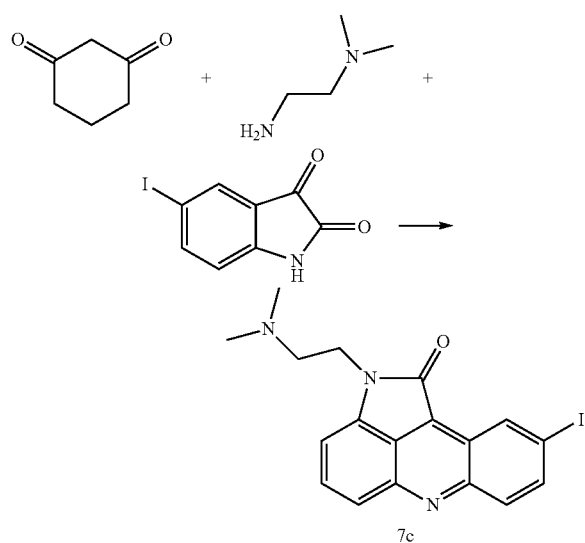

Following the procedure in Example 1, except replace isatin with 5-iodo-isatin, Yield: 24%. $^1$H NMR (400 MHz, CDCl$_3$) δ 9.16 (d, J=1.6 Hz, 1H), 8.03 (dt, J=17.0, 5.5 Hz, 2H), 7.83-7.56 (m, 2H), 6.89 (t, J=6.1 Hz, 1H), 4.06 (t, J=6.9 Hz, 2H), 2.72 (t, J=6.9 Hz, 2H), 2.36 (s, 6H). $^{13}$C NMR (100.6 MHz, CDCl$_3$) δ 167.43, 150.17, 146.48, 140.10, 139.21, 133.29, 132.99, 131.81, 126.63, 123.58, 122.05, 119.74, 105.26, 96.42, 57.48, 45.69, 38.80.

Example 29

Compound 7d: 2-(3-(dimethylamino)propyl)-9-iodopyrrolo[2,3,4-kl]acridin-1-(2H)-one

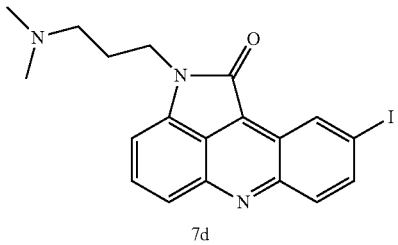

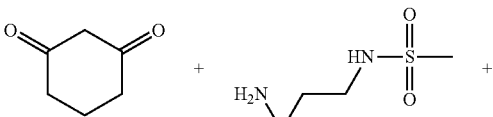

Following the procedure in Example 1, except replace isatin with 5-iodo-isatin, and replace $N^1,N^1$-dimethylethane-1,2-diamine with $N^1,N^1$-dimethylpropane-1,3-diamine. Yield: 35%. $^1$H NMR (400 MHz, CDCl$_3$) δ 9.13 (d, J=1.7 Hz, 1H), 8.07-7.96 (m, 2H), 7.65 (dt, J=9.0, 7.8 Hz, 2H), 6.92 (d, J=6.6 Hz, 1H), 4.02 (t, J=7.0 Hz, 2H), 2.64-2.51 (m, 2H), 2.36 (s, 6H), 2.13-1.99 (m, 2H). $^{13}$C NMR (100.6 MHz, CDCl$_3$) δ 167.50, 150.14, 146.45, 140.01, 139.19, 133.35, 132.90, 131.83, 126.52, 123.51, 122.07, 119.61, 105.43, 96.47, 56.22, 44.79, 38.50, 26.38.

Example 30

Compound 7e: N-(3-(9-methyl-1-oxopyrrolo[2,3,4-kl]acridin-2-(1H)-yl)propyl)methanesulfonamide

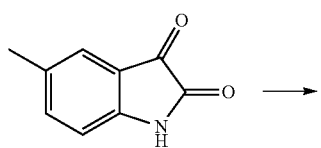

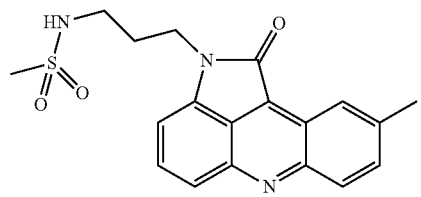

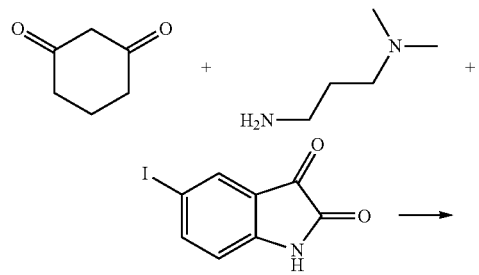

Following the procedure in Example 1, except replace isatin with 5-methyl-isatin, and replace $N^1,N^1$-dimethylethane-1,2-diamine with N-(3-aminopropyl) methanesulfonamide. Yield: 11%. $^1$H NMR (400 MHz, CDCl$_3$) δ 8.49 (s, 1H), 8.35-8.16 (m, 1H), 7.87-7.55 (m, 3H), 6.91 (t, J=6.7 Hz, 1H), 4.11 (t, J=6.3 Hz, 2H), 3.27-3.19 (m, 2H), 3.00 (d, J=5.5 Hz, 3H), 2.64 (s, 3H), 2.15-2.05 (m, 2H).

Example 31

Compound 7f: N-(3-(9-chloro-1-oxopyrrolo[2,3,4-kl]acridin-2-(1H)-yl)propyl) methanesulfonamide

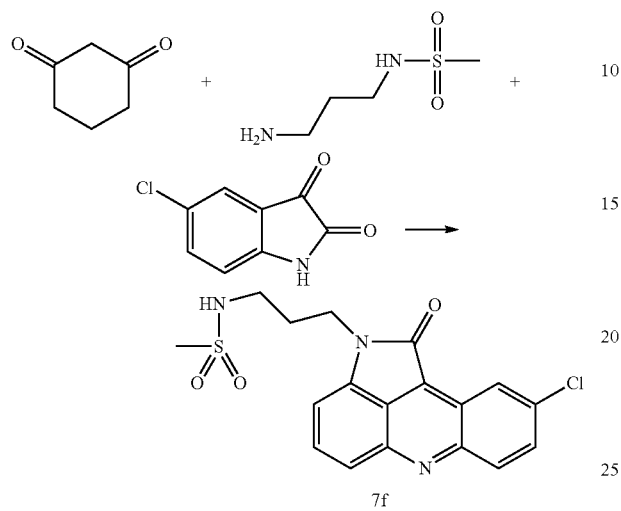

Following the procedure in Example 1, except replace isatin with 5-chloro-isatin, and replace $N^1,N^1$-dimethylethane-1,2-diamine with N-(3-aminopropyl)methanesulfonamide. Yield: 11%. $^1$H NMR (400 MHz, DMSO) δ 8.50 (d, J=2.0 Hz, 1H), 8.30 (d, J=9.3 Hz, 1H), 7.99-7.57 (m, 3H), 7.11 (t, J=5.6 Hz, 1H), 4.00 (dd, J=17.1, 10.1 Hz, 2H), 3.10 (dd, J=12.8, 6.5 Hz, 2H), 2.92 (s, 3H), 1.97 (dd, J=13.9, 6.9 Hz, 2H).

Example 32

Compound 7g: 9-chloro-2-(3-hydroxypropyl)pyrrolo[2,3,4-kl]acridin-1-(2H)-one

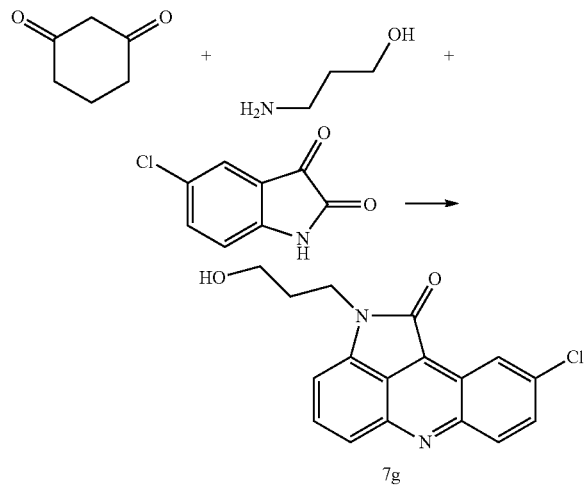

Following the procedure in Example 1, except replace isatin with 5-chloro-isatin, and replace $N^1,N^1$-dimethylethane-1,2-diamine with 3-aminopropan-1-ol. Yield: 20%. $^1$H NMR (400 MHz, CDCl$_3$) δ 8.69 (dd, J=9.5, 2.3 Hz, 1H), 8.24 (d, J=9.3 Hz, 1H), 7.83-7.59 (m, 3H), 6.94 (d, J=6.7 Hz, 1H), 4.21-4.04 (m, 2H), 3.72 (t, J=5.7 Hz, 2H), 2.12-1.97 (m, 2H). $^{13}$C NMR (100.6 MHz, CDCl$_3$) δ 168.28, 149.79, 146.12, 139.70, 135.73, 133.10, 132.02, 131.83, 126.93, 122.72, 122.60, 122.34, 119.76, 105.58, 58.76, 36.88, 31.31.

Contrasting Example 1

Compound 6a: 2-butylpyrrolo[2,3,4-kl]acridin-1-(2H)-one

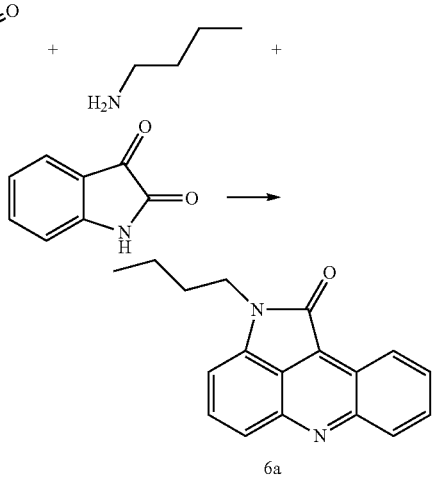

Following the procedure in Example 1, except replace $N^1,N^1$-dimethylethane-1,2-diamine with butan-1-amine. Yield: 52%. $^1$H NMR (400 MHz, CDCl$_3$) δ 8.87 (dd, J=8.5, 0.7 Hz, 1H), 8.40 (d, J=8.8 Hz, 1H), 7.92-7.86 (m, 1H), 7.83-7.75 (m, 2H), 7.68 (dd, J=9.0, 6.8 Hz, 1H), 6.89 (d, J=6.8 Hz, 1H), 3.98 (t, J=7.2 Hz, 2H), 1.88-1.77 (m, 2H), 1.47 (dq, J=14.8, 7.4 Hz, 2H), 0.99 (t, J=7.4 Hz, 3H). $^{13}$C NMR (100.6 MHz, CDCl$_3$) δ 167.86, 151.69, 146.20, 140.27, 132.76, 130.62, 130.40, 128.84, 128.18, 124.06, 122.79, 121.92, 119.60, 104.50, 40.27, 30.93, 20.21, 13.76.

Contrasting Example 2

Compound 6b: 2-phenylpyrrolo[2,3,4-kl]acridin-1-(2H)-one

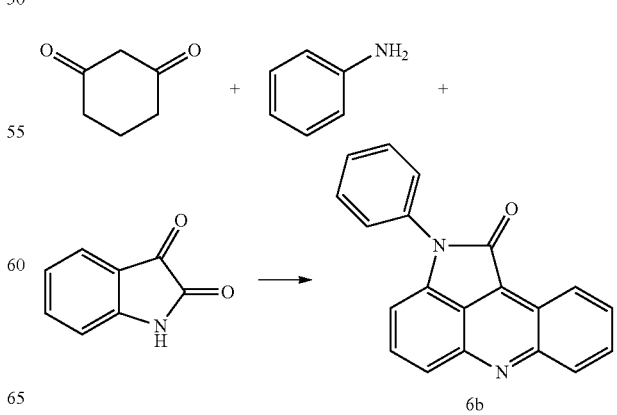

Following the procedure in Example 1, except replace $N^1,N^1$-dimethylethane-1,2-diamine with aniline. Yield: 66%. $^1$H NMR (400 MHz, CDCl$_3$) δ 8.95 (dd, J=8.5, 0.7 Hz, 1H), 8.46 (d, J=8.8 Hz, 1H), 7.94 (ddd, J=16.4, 9.0, 5.3 Hz, 2H), 7.86-7.80 (m, 1H), 7.70 (dd, J=9.0, 6.9 Hz, 1H), 7.67-7.57 (m, 4H), 7.49-7.43 (m, 1H), 7.03 (d, J=6.9 Hz, 1H). $^{13}$C NMR (100.6 MHz, CDCl$_3$) δ 167.12, 151.87, 146.47, 140.05, 134.81, 132.79, 130.76, 130.70, 129.59, 129.25, 127.65, 125.86, 124.14, 123.02, 122.64, 119.77, 105.99.

In Vitro Cytotoxicity Evaluation

Materials and methods: MTT (3-[4,5-dimethylthiazol-2-yl]-diphenyl tetrazolium bromide) method was employed to determine the antiproliferative activity of all the compounds of the Examples and Contrasting Examples in vitro against selected cell lines, including HCT116 (human colon cancer cell), PC-3 (human prostate cancer), HepG2 (human hepatocellular carcinoma), SK-OV-3 (human ovarian adenocarcinoma), MCF-7 (human breast cancer), U87MG (human glioblastoma cell) cell lines.

Procedure: Human tumor cells of HCT116, PC-3, HepG2, SK-OV-3, MCF-7, and U87MG were in vitro cultured, and collected until the cells grow to the logarithmic phase. The cells were centrifuged for 5 minutes at 1000 rpm, and supernatant was discarded. Subsequently appropriate culture medium was added to suspend the precipitation, and the concentration of cells was adjusted to 3.5~5.5×10$^4$/mL. the suspensions of cells were seeded in 96-well microplate at 100 μL per well, and incubated in incubator (37° C., 5% CO$_2$) for 24 hr. The compound to test was added. For the control group, equivalent concentration of DMSO (final concentration 0.5%) was added. For each group, three copy wells were set. After incubated for 72 hr, 20 μL 5 mg/mL of MTT was added into each well, and placed at 37° C. for 3 hr. 150 μL of DMSO was added into each wells, and vibrated the shaker at 37° C. for 5 mins, then measured the absorbance (OD) value at 492 nm/620 nm. The IC50 values were calculated using Prism 5.0 software.

| IC$_{50}$ (μM)/ Compound No. | Cancer cell lines | | | | | |
|---|---|---|---|---|---|---|
| | HCT116 | PC3 | U87MG | HepG2 | SK-OV-3 | MCF-7 |
| 1a | 7.406 | 14.50 | 0.582 | 6.350 | 14.77 | — |
| 1b | 1.867 | 3.010 | 1.779 | 2.778 | 8.432 | — |
| 1f | 1.134 | 3.188 | 3.931 | 2.272 | 3.646 | — |
| 1g | 0.946 | 3.993 | — | 2.161 | 6.523 | — |
| 1h | 1.803 | 11.91 | 10.22 | 8.150 | 11.94 | — |
| 2a | 1.050 | 3.520 | 2.047 | 2.825 | — | — |
| 2b | 0.859 | 1.224 | 1.446 | 1.075 | — | — |
| 2d | 0.951 | 1.853 | 1.697 | 1.408 | — | — |
| 2e | 1.338 | 0.998 | 1.744 | 1.865 | — | — |
| 3a | 1.380 | 8.209 | 2.188 | 2.852 | — | — |
| 3b | 1.322 | 2.328 | 1.578 | 1.467 | — | — |
| 3c | 1.111 | 3.472 | 1.850 | 1.830 | — | — |
| 3d | 1.491 | 4.993 | 2.363 | 2.102 | — | — |
| 4a | 1.418 | 4.134 | 1.326 | 2.573 | — | — |
| 4b | 1.381 | 2.884 | 1.891 | 2.246 | — | — |
| 4c | 0.284 | 1.396 | 0.4966 | 1.502 | — | — |
| 4d | 1.210 | 4.704 | 1.780 | 3.577 | — | — |
| 5a | 1.061 | 2.903 | 1.480 | 1.941 | — | — |
| 5b | 0.930 | 2.239 | 1.266 | 1.173 | — | — |
| 5c | 0.165 | 0.689 | 0.269 | 0.232 | — | — |
| 5d | 1.003 | 2.508 | 1.423 | 1.722 | — | — |
| 5e | 0.767 | 1.661 | 0.959 | 1.281 | — | — |
| 7a | 1.867 | — | — | 1.853 | — | 1.973 |
| 7b | 2.275 | — | — | 3.837 | — | 2.149 |
| 7d | 2.638 | — | — | 3.784 | — | 2.797 |
| 6a | >50 | >50 | >50 | >50 | >50 | — |
| 6b | >50 | >50 | >50 | >50 | >50 | — |

"—" not determined.

Fused acridine derivative carrying an aromatic side chain, such as phenyl; or an alkyl side chain, such as n-butyl, showed no antiproliferative activity. In contrast, fused acridine derivative carrying a side chain containing nitrogen or oxygen, such as a tertiary-amine or a hydroxyl, play important role in the antiproliferative activity, and improve 100-fold than their aryl or alkyl counterparts. These results indicate that the fused acridine derivatives of the invention have achieved unexpected technical effects.

Assay for Inhibiting Cancer Cell Clone Formation

Materials and methods: The tested tumor cells (U87MG) in the logarithmic phase were digested with 0.25% trypsin then percussed gently to the single cell state, and counted the live cells. The cells density was adjusted to 1×10$^6$/L with DMEM containing 20% fetal bovine serum, and then diluted gradiently according to the experiment requirement.

Two concentrations (1.2% and 0.7%) of low melting point agarose fluid were prepared with distilled water respectively. A mixture of 1.2% agarose fluid and 2×DMEM medium (contains 2× antibiotics and 20% calf serum) was prepared in 1:1 ratio, then transferred (3 mL) into 6 cm diameter flat dishes, cooled to solidification to furnish the bottom agar which was stored in a CO$_2$ incubator. The cell suspension (0.2 mL) was added to a mixture of 0.7% agarose and 2×DMEM medium which was prepared in 1:1 ratio in sterile tubes, and thoroughly mixed before injection to the pre-coated dishes to form the double layer agar. After the upper agar being solidified, the dishes were incubated in 37° C. and 5% CO$_2$ for 10-14 days, each experiment was performed in 3-6 times.

The number of clones was counted under an inverted microscope. The clone formation rate was calculated.

The results: The compounds of this invention, 2b、2d、3a'、3b'、5a、5b、5c'、5d, and 5e significantly inhibited glioma cell clone formation on the concentration range from 0.020 to 0.090 μM.

In Vivo Antitumor Activity Test

Animals: Female 6-8 weeks BALB/c nude mice weighed 16 to 18 g. They were raised at SPF-level animal room with a 12 h light-dark cycle; drinking and eating were provided ad libitum.

Animal Grouping and Dosage Regimen

| Groups | Animals | Dosage (mg/kg) | Dose volume (ml/10 g) | Dosing frequency |
|---|---|---|---|---|
| Saline(vehicle) | 12 | — | 0.1 | qd × 5/w |
| TMZ (positive) | 6 | 50 | | qd × 5/w |
| 5c' (low dose) | 6 | 20 | | qd × 5/w |
| 5c' (medium dose) | 6 | 40 | | qd × 5/w |
| 5c' (high dose) | 6 | 80 | | qd × 5/w |

Procedures

Under aseptic conditions, U87MG cells in the logarithmic phase were digested and its density was adjusted. U87MG cells were inoculated hypodermically in BALB/c nude mice, 0.1 mL for each mouse. The diameter of the transplantation was measured with a Vernier caliper. After their tumor size was about 100-200 mm³, 36 mice were randomly divided into 5 groups according to the tumor size. The mice of each group was orally administered the dose respectively according to the above-mentioned schedule, and the mice of the vehicle group were given same dose of saline. The first day of dosing named for D1. The long diameter and short diameter of the tumor size of each mouse were measured twice a week, and the body weights were recorded at the same time.

Antitumor Efficacy Evaluation Indicators

Indicators were observed, measured, and recorded from the first day of dosing. The tumor size was measured using a Vernier caliper to calculate tumor volume change and the tumor growth. After the tumor-burdened mice were executed and dissected, the tumor tissues were separated, and weighed.

Indicators for antitumor efficacy evaluation including: relative tumor inhibition rate, body weight, general state of the mice and related toxicity index. Curves of tumor growth and body weight change of every group were plotted at the end of the experiment.

The calculation formula for tumor volume (TV) is: $TV=\frac{1}{2} \times a \times b^2$, where a and b means long diameter and short diameter of the tumor size respectively.

The compound was proved efficacy when the tumor weight (TW) of the drug treatment group is lower than that of the control group, and the statistical test P<0.05. Tumor inhibition rate IR (%)=(1−TTW/CTW)×100%, TTW: TW of the treatment group; CTW: TW of the control group.

Statistical analysis: Data were analyzed using SPSS 11.0 with Student t-test for comparisons and ANOVA. P-values <0.05 were considered significant.

The results: After the subcutaneous injection of U87MG cells, the tumor grew slowly. At day 26, the mice were divided into 5 groups. Temozolomide (TMZ), saline, and compound 5c' were intragastricly administered on a 5 days a week, and day 6, day 7 withdrawal schedule. At the end of the test, 10 doses were administered in total. The animal weight of the TMZ group was significant lower compared with the vehicle. The animal weights of median and high dose group of 5c' grew slowly compared with the vehicle; even animal weight loss of the high dose group (80 mg/kg) was significantly lower than the positive control (TMZ) group. The tumor inhibition rate (IR) were 69% and 91%, respectively, indicated that the tumor size of the median and high dose group of compound 5c' was significantly smaller than the vehicle respectively.

Industrial Practicability

The present invention provides fused acridine derivatives with significantly antiproliferative effect against a variety of tumor cell lines, may be used as anticancer drugs.

The invention claimed is:

1. A fused acridine derivative of the formula (I):

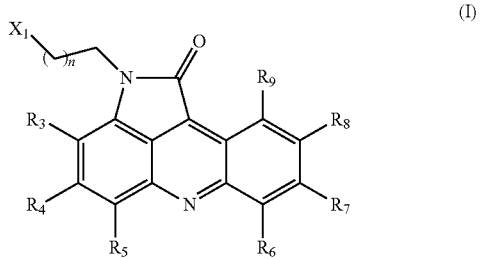

or pharmaceutically acceptable acid addition salt, or solvate thereof, wherein, n is an integer from 0 to 6;

$R_3$, $R_4$, $R_5$, $R_6$, $R_7$, $R_8$ and $R_9$ are each independently selected from the group consisting of hydrogen, hydroxy, $C_{1-4}$ alkyl, $C_{1-4}$ alkoxy, halogen, nitro and cyano;

$X_1$ is hydroxy or —$NR_1R_2$, wherein —$NR_1R_2$ is the following formula:

$R_1$ and $R_2$ are each independently selected from hydrogen, $C_{1-4}$ alkyl or substituted $C_{1-4}$ alkyl, $C_{1-4}$ alkyl sulfonyl or $R_1$ and $R_2$ together with the Nitrogen to which they are attached form a nitrogen-containing 4 to 6 membered heterocyclic ring.

2. A fused acridine derivative of claim 1, or pharmaceutically acceptable acid addition salt or solvate thereof, wherein, n is 1, 2 or 3.

3. A fused acridine derivative of claim 1, or pharmaceutically acceptable acid addition salt or solvate thereof, wherein, $X_1$ is hydroxy or —$NR_1R_2$, $R_1$ and $R_2$ together with the N to which they are attached form a nitrogen-containing 4 to 6 membered heterocyclic ring, and the nitrogen-containing 4 to 6 membered heterocyclic rings is selected from 4, 5 or 6 membered Nitrogen heterocyclic which can optionally be substituted by one or more of the following substituents selected from hydroxyl, amido, sulfamido, $C_{1-4}$ alkyl, $C_{1-4}$ alkoxy, halogen, nitro or cyano.

4. A fused acridine derivative of claim 3, or pharmaceutically acceptable acid addition salt or solvate thereof, wherein, $R_1$ and $R_2$ together with the N to which they are attached form nitrogen-containing 4 to 6 membered heterocyclic rings which are selected from azetidine, pyrrolidine, pyrrole, imidazole, piperidine, piperazine or morpholine.

5. The fused acridine derivative of claim 1, or pharmaceutically acceptable acid addition salt or solvate thereof, wherein, R3, R4, R5, R6, R7, R8 and R9 are each independently hydrogen, hydroxy, methyl, methoxy, fluorine, chlorine, bromine, iodine, nitro or cyano, or wherein R5, R6 and R8 are each independently hydrogen, hydroxy, methyl, methoxy, fluorine, chlorine, bromine, iodine, nitro or cyano, and R3, R4, R7 and R9 are hydrogen.

6. A fused acridine derivative of claim 1, or pharmaceutically acceptable acid addition salt or solvate thereof, which is selected from the group consisting of:

2-(2-(dimethylamino)ethyl)pyrrolo [2,3,4-kl]acridin-1-(2H)-one 2-(3-morpholinopropyl)pyrrolo[2,3,4-kl]acridin-1-(2H)-one 2-(2-morpholinoethyl)pyrrolo [2,3,4-kl]acridin-1-(2H)-one 2-(2-(piperidin-1-yl)ethyl)pyrrolo[2,3,4-kl]acridin-1-(2H)-one 2-(2-(pyrrolidin-1-yl)ethyl)pyrrolo[2,3,4-kl]acridin-1-(2H)-one 2-(3-(pyrrolidin-1-yl)propyl)pyrrolo[2,3,4-kl]acridin-1-(2H)-one 2-(2-(dimethylamino)ethyl)-9-methylpyrrolo [2,3,4-kl]acridin-1-(2H)-one 9-chloro-2-(2-(dimethylamino)ethyl)pyrrolo [2,3,4-kl] acridin-1-(2H)-one
2-(2-(dimethylamino)ethyl)-9-methoxypyrrolo [2,3,4-kl] acridin-1-(2H)-one
2-(2-(dimethylamino)ethyl)-7-fluoropyrrolo [2,3,4-kl] acridin-1-(2H)-one
2-(2-(dimethylamino)propyl)-5-nitropyrrolo [2,3,4-kl] acridin-1-(2H)-one
2-(3-(dimethylamino)propyl)-9-methylpyrrolo[2,3,4-kl] acridin-1-(2H)-one
9-chloro-2-(3-(dimethylamino)propyl)pyrrolo[2,3,4-kl] acridin-1-(2H)-one
9-chloro-2-(3-(dimethylamino)propyl)pyrrolo[2,3,4-kl] acridin-1-(2H)-one fumarate
2-(3-(dimethylamino)propyl)-9-methoxypyrrolo[2,3,4-kl]acridin-1-(2H)-one
2-(3-(dimethylamino)propyl)-7-fluoropyrrolo[2,3,4-kl] acridin-1-(2H)-one
9-methyl-2-(2-(piperidin-1-yl)ethyl)pyrrolo[2,3,4-kl] acridin-1-(2H)-one
9-chloro-2-(2-(piperidin-1-yl)ethyl)pyrrolo[2,3,4-kl]acridin-1-(2H)-one
9-methoxy-2-(2-(piperidin-1-yl)ethyl)pyrrolo[2,3,4-kl] acridin-1-(2H)-one
7-fluoro-2-(2-(piperidin-1-yl)ethyl)pyrrolo[2,3,4-kl]acridin-1-(2H)-one
2-(2-(dimethylamino)ethyl)-5,9-dimethylpyrrolo[2,3,4-kl]acridin-1-(2H)-one
9-chloro-2-(2-(dimethylamino)ethyl)-5-methylpyrrolo[2,3,4-kl]acridin-1-(2H)-one
2-(2-(dimethylamino)ethyl)-9-methoxy-5-methylpyrrolo [2,3,4-kl]acridin-1-(2H)-one
2-(2-(dimethylamino)ethyl)-9-methoxy-5-methylpyrrolo [2,3,4-kl]acridin-1-(2H)-one fumarate
2-(2-(dimethylamino)ethyl)-7-fluoro-5-methylpyrrolo[2,3,4-kl]acridin-1-(2H)-one
2-(2-(dimethylamino)ethyl)-5-methylpyrrolo[2,3,4-kl] acridin-1-(2H)-one
9-bromo-2-(2-(dimethylamino)ethyl)pyrrolo[2,3,4-kl] acridin-1-(2H)-one
9-bromo-2-(3-(dimethylamino)propyl)pyrrolo[2,3,4-kl] acridin-1-(2H)-one
2-(2-(dimethylamino)ethyl)-9-iodo-pyrrolo[2,3,4-kl]acridin-1-(2H)-one
2-(3-(dimethylamino)propyl)-9-iodopyrrolo[2,3,4-kl] acridin-1-(2H)-one
N-(3-(9-methyl-1-oxopyrrolo[2,3,4-kl]acridin-2-(1H)-yl) propyl)methanesulfonamide
N-(3-(9-chloro-1-oxopyrrolo[2,3,4-kl]acridin-2-(1H)-yl) propyl)methanesulfonamide
9-chloro-2-(3-hydroxypropyl)pyrrolo[2,3,4-kl]acridin-1-(2H)-one.

7. A pharmaceutical composition comprising the fused acridine derivatives as claimed in claim 1.

8. A pharmaceutical composition comprising the fused acridine derivatives as claimed in claim 2.

9. A pharmaceutical composition comprising the fused acridine derivatives as claimed in claim 3.

10. A pharmaceutical composition comprising the fused acridine derivatives as claimed in claim 4.

11. A pharmaceutical composition comprising the fused acridine derivatives as claimed in claim 5.

12. A pharmaceutical composition comprising the fused acridine derivatives as claimed in claim 6.

13. A process for preparing a fused acridine derivative as claimed in claim 1, including: reacting compounds of formula (III), formula (IV) and formula (V) to afford a compound of formula (I):

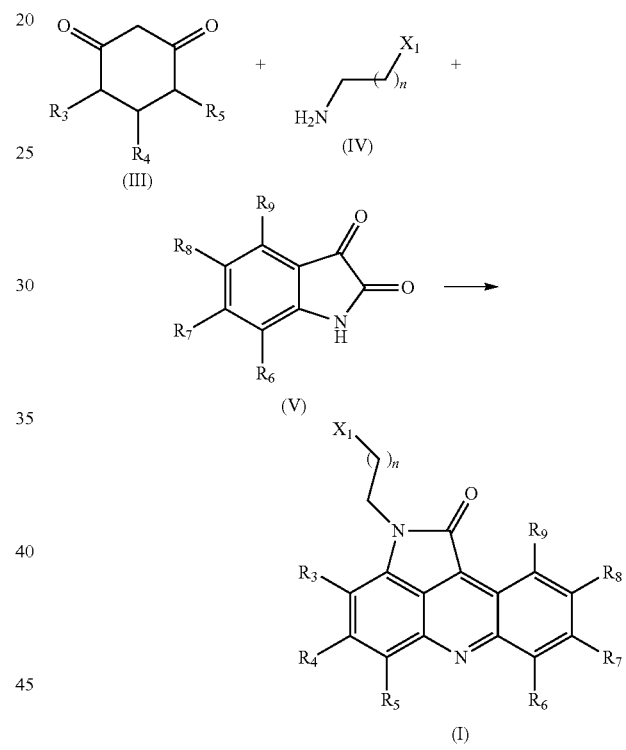

wherein, the substituents of $X_1$, $R_3$, $R_4$, $R_5$, $R_6$, $R_7$, $R_8$, and $R_9$, and n are defined as claimed in claim 1.